US011357819B2

(12) United States Patent
Sugihara et al.

(10) Patent No.: US 11,357,819 B2
(45) Date of Patent: Jun. 14, 2022

(54) CYTOCIDAL AGENT

(71) Applicant: FUJITA ACADEMY, Aichi (JP)

(72) Inventors: Kazuhiro Sugihara, Nagoya (JP);
Naohiro Kanayama, Hamamatsu (JP);
Yuichiro Onodera, Hokkaido (JP);
Toshiaki Shibata, Hamamatsu (JP);
Michiko Fukuda, San Diego, CA (US);
Motohiro Nonaka, Kyoto (JP)

(73) Assignee: FUJITA ACADEMY, Aichi (JP)

( * ) Notice: Subject to any disclaimer, the term of this patent is extended or adjusted under 35 U.S.C. 154(b) by 54 days.

(21) Appl. No.: 16/640,248

(22) PCT Filed: Aug. 23, 2018

(86) PCT No.: PCT/JP2018/031136
§ 371 (c)(1),
(2) Date: Feb. 19, 2020

(87) PCT Pub. No.: WO2019/039540
PCT Pub. Date: Feb. 28, 2019

(65) Prior Publication Data
US 2020/0289608 A1    Sep. 17, 2020

(30) Foreign Application Priority Data
Aug. 24, 2017 (JP) .............................. JP2017-161556

(51) Int. Cl.
*A61K 38/10* (2006.01)
*A61K 47/66* (2017.01)
*A61P 35/00* (2006.01)

(52) U.S. Cl.
CPC .............. *A61K 38/10* (2013.01); *A61K 47/66* (2017.08); *A61P 35/00* (2018.01)

(58) Field of Classification Search
CPC ........... A61K 38/10; A61K 47/66; C07K 7/08
See application file for complete search history.

(56) References Cited

U.S. PATENT DOCUMENTS

| 5,595,756 | A  | 1/1997  | Bally et al.    |
| 9,107,878 | B2 | 8/2015  | Holaday         |
| 9,783,576 | B2 | 10/2017 | Fukuda et al.   |
| 2016/0145308 | A1 | 5/2016  | Fukuda et al.   |
| 2016/0192626 | A1 | 7/2016  | Kajitani et al. |
| 2017/0290882 | A1 | 10/2017 | Andronova et al. |
| 2017/0360955 | A1 | 12/2017 | Janssen et al.  |

FOREIGN PATENT DOCUMENTS

| JP | 2013-523824 A    | 6/2013  |
| JP | 66-13499 B2      | 12/2019 |
| WO | WO 2007/076501 A2 | 7/2007  |
| WO | WO 2011/027312 A1 | 3/2011  |
| WO | WO 2011/079304 A1 | 6/2011  |
| WO | WO-2011079304 A1 * | 6/2011  | ............ A61K 47/64 |
| WO | WO-2014201118 A2 * | 12/2014 | ............ A61K 38/08 |
| WO | WO 2015/041019 A1 | 3/2015  |
| WO | WO 2019/039540 A1 | 2/2019  |

OTHER PUBLICATIONS

International Search Report in related PCT Application PCT/JP2018/031136, dated Oct. 30, 2018, (4 pages) with English translation.
Shibata et al., "Anti-tumor drugs using peptide that mimics sugar chains", Journal of Japan Society of Obstetrics and Gynecology, Acta Obstetrica et Gynaecologica Japonica, 2016, vol. 68, No. 2, p. 858, P3-14-1, ISSN: 0300-9165.
Sugihara et al., "Development of pro-apoptotic peptides as potential therapy for peritoneal endometriosis", Nature Communications, 2014, vol. 5: 4478, DOI:10.1038/ncomms5478, pp. 1-9, ISSN:2041-1723.
Sugihara et al., Search of peptide therapeutic drugs for endometriosis, Programs and abstract of the $32^{nd}$ Annual Meeting of the japan Society of Drug Delivery System, 2016, p. 170, 2-C-20.
Zeng-Ying Qiao et al., Reconfigurable Peptide Nanotherapeutics at Tumor Microenvironmental pH, ACS Appl. Mater. Interfaces, Sep. 2017, pp. 30426-30436.
U.S. Appl. No. 16/960,417 2020/0330549, filed Jul. 7, 2020 Oct. 22, 2020, Kazuhiro Sugihara.
European Search Report for European Patent Application No. 18848077.6, dated May 17, 2021.
Hatakeyama et al., "Targeted drug delivery to tumor vasculature by a carbohydrate mimetic peptide", PNAS, Dec. 6, 2011, 108(49): 19587-19592.
Auerbach et al., "Angiogenesis assays: Problems and pitfalls," Cancer and Metastasis Reviews, 2000, 19: 167-172. (Year: 2000).
Liu et al., "Endometriosis", Merck manual, pp. 1-7. Accessed Apr. 13, 2021.
Gura, "Systems for Identifying New Drugs are Often Faulty," Science, Nov. 1997, 278: 1041-1042. (Year: 1997).
Hait, "Anticancer drug development: the grand challenges," Nature Reviews, Apr. 9, 2020: 253-254. (Year: 2010).
International Preliminary Report on Patentability for PCT International Patent Application No. PCT/JP2018/048523, dated May 12, 2020.
International Search Report for PCT International Patent Application No. PCT/JP2018/048523, dated Mar. 12, 2019.

(Continued)

*Primary Examiner* — Christina Bradley
(74) *Attorney, Agent, or Firm* — Lathrop GPM LLP; Brian C. Trinque; Rebecca L. Wright

(57) ABSTRACT

The present invention is a cytocidal agent including a peptide consisting of an amino acid sequence represented by SEQ ID NO: 1 and a site selectively binding to a target molecule, in which the peptide consisting of an amino acid sequence represented by SEQ ID NO: 1 is a peptide exclusively consisting of L-amino acids, a peptide in which, in amino acid sequences represented by SEQ ID NO: 1, the first to the $14^{th}$ amino acids are D-amino acids, and the $15^{th}$ to $19^{th}$ amino acids are L-amino acids, a peptide in which, in amino acid sequences represented by SEQ ID NO: 1, the first to $14^{th}$ amino acids are L-amino acids, and the $15^{th}$ to the $19^{th}$ amino acids are D-amino acids, or a peptide exclusively consisting of D-amino acids.

10 Claims, 13 Drawing Sheets

Specification includes a Sequence Listing.

(56) References Cited

OTHER PUBLICATIONS

Jain, "Barriers to Drug Delivery in Solid Tumors," Scientific American, Jul. 1994, 58-65. (Year: 1994).
Neidel, Cancer Drug Design and Discovery, Elsevier/Academic Press, 2008, 427-431.
Ramirez et al., "Ovarian Cancer", Merck manual, pp. 1-12. Accessed Apr. 13, 2021.
Proliferation from Merck manual, pp. 1-4. Accessed Apr. 13, 2021.
Sporn et al, "Chemoprevention of cancer," Carcinogenesis, 2000, 21(3): 525-530.
Sugihara et al., "Development of pro-apoptotic peptides as potential therapy for peritoneal endometriosis", Nature Communications, 2014, 5(4478): 1-9.
Sugihara, "Peptide drug discovery" (non-official translation), Journal of Japan Society of Endometriosis, 2015, vol. 36, pp. 38-40.

\* cited by examiner

SEQUENCE LISTING

<160> NUMBER OF SEQ ID NOS: 42

<210> SEQ ID NO 1
<211> LENGTH: 19
<212> TYPE: PRT
<213> ORGANISM: Artificial Sequence
<220> FEATURE:
<223> OTHER INFORMATION: Effector peptide

<400> SEQUENCE: 1

Lys Leu Ala Lys Leu Ala Lys Lys Leu Ala Lys Leu Ala Lys His Leu
1               5                   10                  15

Ala His Leu

<210> SEQ ID NO 2

```
<211> LENGTH: 9
<212> TYPE: PRT
<213> ORGANISM: Artificial Sequence
<220> FEATURE:
<223> OTHER INFORMATION: CNGB3 binding peptide
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 2

Val Arg Arg Ala Xaa Asn Xaa Pro Gly
1               5

<210> SEQ ID NO 3
<211> LENGTH: 9
<212> TYPE: PRT
<213> ORGANISM: Artificial Sequence
<220> FEATURE:
<223> OTHER INFORMATION: Z13 peptide

<400> SEQUENCE: 3

Val Arg Arg Ala Asp Asn Arg Pro Gly
1               5

<210> SEQ ID NO 4
<211> LENGTH: 9
<212> TYPE: PRT
<213> ORGANISM: Artificial Sequence
<220> FEATURE:
<223> OTHER INFORMATION: CNGB3 binding peptide

<400> SEQUENCE: 4

Val Arg Arg Ala Glu Asn Arg Pro Gly
1               5

<210> SEQ ID NO 5
<211> LENGTH: 9
<212> TYPE: PRT
<213> ORGANISM: Artificial Sequence
<220> FEATURE:
<223> OTHER INFORMATION: CNGB3 binding peptide

<400> SEQUENCE: 5

Val Arg Arg Ala Asn Asn Leu Pro Gly
1               5

<210> SEQ ID NO 6
<211> LENGTH: 9
<212> TYPE: PRT
<213> ORGANISM: Artificial Sequence
<220> FEATURE:
<223> OTHER INFORMATION: CNGB3 binding peptide

<400> SEQUENCE: 6

Val Arg Arg Ala Asn Asn Arg Pro Gly
1               5

<210> SEQ ID NO 7
<211> LENGTH: 7
<212> TYPE: PRT
<213> ORGANISM: Artificial Sequence
<220> FEATURE:
<223> OTHER INFORMATION: IF7 peptide
```

-continued

```
<400> SEQUENCE: 7

Ile Phe Leu Leu Trp Gln Arg
1               5

<210> SEQ ID NO 8
<211> LENGTH: 37
<212> TYPE: PRT
<213> ORGANISM: Artificial Sequence
<220> FEATURE:
<223> OTHER INFORMATION: KLAK(14)-HLAH(14)-Z13 peptide

<400> SEQUENCE: 8

Lys Leu Ala Lys Leu Ala Lys Lys Leu Ala Lys Leu Ala Lys His Leu
1               5                   10                  15

Ala His Leu Ala His His Leu Ala His Leu Ala His Val Arg Arg Ala
            20                  25                  30

Asp Asn Arg Pro Gly
        35

<210> SEQ ID NO 9
<211> LENGTH: 37
<212> TYPE: PRT
<213> ORGANISM: Artificial Sequence
<220> FEATURE:
<223> OTHER INFORMATION: KLAK(14)-HLAH(14)-D5E peptide

<400> SEQUENCE: 9

Lys Leu Ala Lys Leu Ala Lys Lys Leu Ala Lys Leu Ala Lys His Leu
1               5                   10                  15

Ala His Leu Ala His His Leu Ala His Leu Ala His Val Arg Arg Ala
            20                  25                  30

Glu Asn Arg Pro Gly
        35

<210> SEQ ID NO 10
<211> LENGTH: 36
<212> TYPE: PRT
<213> ORGANISM: Artificial Sequence
<220> FEATURE:
<223> OTHER INFORMATION: KLAK(14)-HLAH(13)-Z13 peptide

<400> SEQUENCE: 10

Lys Leu Ala Lys Leu Ala Lys Lys Leu Ala Lys Leu Ala Lys His Leu
1               5                   10                  15

Ala His Leu Ala His His Leu Ala His Leu Ala Val Arg Arg Ala Asp
            20                  25                  30

Asn Arg Pro Gly
        35

<210> SEQ ID NO 11
<211> LENGTH: 35
<212> TYPE: PRT
<213> ORGANISM: Artificial Sequence
<220> FEATURE:
<223> OTHER INFORMATION: KLAK(14)-HLAH(12)-Z13 peptide

<400> SEQUENCE: 11

Lys Leu Ala Lys Leu Ala Lys Lys Leu Ala Lys Leu Ala Lys His Leu
1               5                   10                  15

Ala His Leu Ala His His Leu Ala His Leu Val Arg Arg Ala Asp Asn
            20                  25                  30

Arg Pro Gly
```

```
<210> SEQ ID NO 12
<211> LENGTH: 34
<212> TYPE: PRT
<213> ORGANISM: Artificial Sequence
<220> FEATURE:
<223> OTHER INFORMATION: KLAK(14)-HLAH(11)-Z13 peptide

<400> SEQUENCE: 12

Lys Leu Ala Lys Leu Ala Lys Lys Leu Ala Lys Leu Ala Lys His Leu
1               5                   10                  15

Ala His Leu Ala His His Leu Ala His Val Arg Arg Ala Asp Asn Arg
            20                  25                  30

Pro Gly

<210> SEQ ID NO 13
<211> LENGTH: 33
<212> TYPE: PRT
<213> ORGANISM: Artificial Sequence
<220> FEATURE:
<223> OTHER INFORMATION: KLAK(14)-HLAH(10)-Z13 peptide

<400> SEQUENCE: 13

Lys Leu Ala Lys Leu Ala Lys Lys Leu Ala Lys Leu Ala Lys His Leu
1               5                   10                  15

Ala His Leu Ala His His Leu Ala Val Arg Arg Ala Asp Asn Arg Pro
            20                  25                  30

Gly

<210> SEQ ID NO 14
<211> LENGTH: 32
<212> TYPE: PRT
<213> ORGANISM: Artificial Sequence
<220> FEATURE:
<223> OTHER INFORMATION: KLAK(14)-HLAH(9)-Z13 peptide

<400> SEQUENCE: 14

Lys Leu Ala Lys Leu Ala Lys Lys Leu Ala Lys Leu Ala Lys His Leu
1               5                   10                  15

Ala His Leu Ala His His Leu Val Arg Arg Ala Asp Asn Arg Pro Gly
            20                  25                  30

<210> SEQ ID NO 15
<211> LENGTH: 31
<212> TYPE: PRT
<213> ORGANISM: Artificial Sequence
<220> FEATURE:
<223> OTHER INFORMATION: KLAK(14)-HLAH(8)-Z13 peptide

<400> SEQUENCE: 15

Lys Leu Ala Lys Leu Ala Lys Lys Leu Ala Lys Leu Ala Lys His Leu
1               5                   10                  15

Ala His Leu Ala His His Val Arg Arg Ala Asp Asn Arg Pro Gly
            20                  25                  30

<210> SEQ ID NO 16
<211> LENGTH: 30
<212> TYPE: PRT
<213> ORGANISM: Artificial Sequence
<220> FEATURE:
<223> OTHER INFORMATION: KLAK(14)-HLAH(7)-Z13 peptide

<400> SEQUENCE: 16
```

```
Lys Leu Ala Lys Leu Ala Lys Lys Leu Ala Lys Leu Ala Lys His Leu
1               5                   10                  15

Ala His Leu Ala His Val Arg Arg Ala Asp Asn Arg Pro Gly
            20                  25                  30

<210> SEQ ID NO 17
<211> LENGTH: 37
<212> TYPE: PRT
<213> ORGANISM: Artificial Sequence
<220> FEATURE:
<223> OTHER INFORMATION: HLAH(14)-KLAK(14)-Z13 peptide

<400> SEQUENCE: 17

His Leu Ala His Leu Ala His His Leu Ala His Leu Ala His Lys Leu
1               5                   10                  15

Ala Lys Leu Ala Lys Lys Leu Ala Lys Leu Ala Lys Val Arg Arg Ala
            20                  25                  30

Asp Asn Arg Pro Gly
            35

<210> SEQ ID NO 18
<211> LENGTH: 36
<212> TYPE: PRT
<213> ORGANISM: Artificial Sequence
<220> FEATURE:
<223> OTHER INFORMATION: HLAH(14)-KLAK(13)-Z13 peptide

<400> SEQUENCE: 18

His Leu Ala His Leu Ala His His Leu Ala His Leu Ala His Lys Leu
1               5                   10                  15

Ala Lys Leu Ala Lys Lys Leu Ala Lys Leu Ala Val Arg Arg Ala Asp
            20                  25                  30

Asn Arg Pro Gly
            35

<210> SEQ ID NO 19
<211> LENGTH: 35
<212> TYPE: PRT
<213> ORGANISM: Artificial Sequence
<220> FEATURE:
<223> OTHER INFORMATION: HLAH(14)-KLAK(13)-Z13 peptide

<400> SEQUENCE: 19

His Leu Ala His Leu Ala His His Leu Ala His Leu Ala His Lys Leu
1               5                   10                  15

Ala Lys Leu Ala Lys Lys Leu Ala Lys Leu Val Arg Arg Ala Asp Asn
            20                  25                  30

Arg Pro Gly
            35

<210> SEQ ID NO 20
<211> LENGTH: 34
<212> TYPE: PRT
<213> ORGANISM: Artificial Sequence
<220> FEATURE:
<223> OTHER INFORMATION: HLAH(14)-KLAK(13)-Z13 peptide

<400> SEQUENCE: 20

His Leu Ala His Leu Ala His His Leu Ala His Leu Ala His Lys Leu
1               5                   10                  15

Ala Lys Leu Ala Lys Lys Leu Ala Lys Val Arg Arg Ala Asp Asn Arg
            20                  25                  30
```

Pro Gly

<210> SEQ ID NO 21
<211> LENGTH: 33
<212> TYPE: PRT
<213> ORGANISM: Artificial Sequence
<220> FEATURE:
<223> OTHER INFORMATION: HLAH(14)-KLAK(13)-Z13 peptide

<400> SEQUENCE: 21

His Leu Ala His Leu Ala His His Leu Ala His Leu Ala His Lys Leu
1               5                   10                  15

Ala Lys Leu Ala Lys Lys Leu Ala Val Arg Arg Ala Asp Asn Arg Pro
            20                  25                  30

Gly

<210> SEQ ID NO 22
<211> LENGTH: 32
<212> TYPE: PRT
<213> ORGANISM: Artificial Sequence
<220> FEATURE:
<223> OTHER INFORMATION: HLAH(14)-KLAK(13)-Z13 peptide

<400> SEQUENCE: 22

His Leu Ala His Leu Ala His His Leu Ala His Leu Ala His Lys Leu
1               5                   10                  15

Ala Lys Leu Ala Lys Lys Leu Val Arg Arg Ala Asp Asn Arg Pro Gly
            20                  25                  30

<210> SEQ ID NO 23
<211> LENGTH: 31
<212> TYPE: PRT
<213> ORGANISM: Artificial Sequence
<220> FEATURE:
<223> OTHER INFORMATION: HLAH(14)-KLAK(13)-Z13 peptide

<400> SEQUENCE: 23

His Leu Ala His Leu Ala His His Leu Ala His Leu Ala His Lys Leu
1               5                   10                  15

Ala Lys Leu Ala Lys Lys Val Arg Arg Ala Asp Asn Arg Pro Gly
            20                  25                  30

<210> SEQ ID NO 24
<211> LENGTH: 30
<212> TYPE: PRT
<213> ORGANISM: Artificial Sequence
<220> FEATURE:
<223> OTHER INFORMATION: HLAH(14)-KLAK(13)-Z13 peptide

<400> SEQUENCE: 24

His Leu Ala His Leu Ala His His Leu Ala His Leu Ala His Lys Leu
1               5                   10                  15

Ala Lys Leu Ala Lys Val Arg Arg Ala Asp Asn Arg Pro Gly
            20                  25                  30

<210> SEQ ID NO 25
<211> LENGTH: 29
<212> TYPE: PRT
<213> ORGANISM: Artificial Sequence
<220> FEATURE:
<223> OTHER INFORMATION: KLAK(14)-HLAH(6)-Z13 peptide

<400> SEQUENCE: 25

```
Lys Leu Ala Lys Leu Ala Lys Lys Leu Ala Lys Leu Ala Lys His Leu
1               5                   10                  15

Ala His Leu Ala Val Arg Arg Ala Asp Asn Arg Pro Gly
            20                  25
```

<210> SEQ ID NO 26
<211> LENGTH: 28
<212> TYPE: PRT
<213> ORGANISM: Artificial Sequence
<220> FEATURE:
<223> OTHER INFORMATION: KLAK(14)-HLAH(5)-Z13 peptide

<400> SEQUENCE: 26

```
Lys Leu Ala Lys Leu Ala Lys Lys Leu Ala Lys Leu Ala Lys His Leu
1               5                   10                  15

Ala His Leu Val Arg Arg Ala Asp Asn Arg Pro Gly
            20                  25
```

<210> SEQ ID NO 27
<211> LENGTH: 27
<212> TYPE: PRT
<213> ORGANISM: Artificial Sequence
<220> FEATURE:
<223> OTHER INFORMATION: KLAK(14)-HLAH(4)-Z13 peptide

<400> SEQUENCE: 27

```
Lys Leu Ala Lys Leu Ala Lys Lys Leu Ala Lys Leu Ala Lys His Leu
1               5                   10                  15

Ala His Val Arg Arg Ala Asp Asn Arg Pro Gly
            20                  25
```

<210> SEQ ID NO 28
<211> LENGTH: 27
<212> TYPE: PRT
<213> ORGANISM: Artificial Sequence
<220> FEATURE:
<223> OTHER INFORMATION: KLAK(14)-HLAH(3)-Z13 peptide

<400> SEQUENCE: 28

```
Lys Leu Ala Lys Leu Ala Lys Lys Leu Ala Lys Leu Ala Lys His Leu
1               5                   10                  15

Ala His Val Arg Arg Ala Asp Asn Arg Pro Gly
            20                  25
```

<210> SEQ ID NO 29
<211> LENGTH: 25
<212> TYPE: PRT
<213> ORGANISM: Artificial Sequence
<220> FEATURE:
<223> OTHER INFORMATION: KLAK(14)-HLAH(2)-Z13 peptide

<400> SEQUENCE: 29

```
Lys Leu Ala Lys Leu Ala Lys Lys Leu Ala Lys Leu Ala Lys His Leu
1               5                   10                  15

Val Arg Arg Ala Asp Asn Arg Pro Gly
            20                  25
```

<210> SEQ ID NO 30
<211> LENGTH: 24
<212> TYPE: PRT
<213> ORGANISM: Artificial Sequence
<220> FEATURE:
<223> OTHER INFORMATION: KLAK(14)-HLAH(1)-Z13 peptide

<400> SEQUENCE: 30

```
Lys Leu Ala Lys Leu Ala Lys Lys Leu Ala Lys Leu Ala Lys His Val
1               5                   10                  15

Arg Arg Ala Asp Asn Arg Pro Gly
            20
```

<210> SEQ ID NO 31
<211> LENGTH: 29
<212> TYPE: PRT
<213> ORGANISM: Artificial Sequence
<220> FEATURE:
<223> OTHER INFORMATION: KLAK(13)-HLAH(7)-Z13 peptide

<400> SEQUENCE: 31

```
Lys Leu Ala Lys Leu Ala Lys Lys Leu Ala Lys Leu Ala His Leu Ala
1               5                   10                  15

His Leu Ala His Val Arg Arg Ala Asp Asn Arg Pro Gly
            20                  25
```

<210> SEQ ID NO 32
<211> LENGTH: 28
<212> TYPE: PRT
<213> ORGANISM: Artificial Sequence
<220> FEATURE:
<223> OTHER INFORMATION: KLAK(12)-HLAH(7)-Z13 peptide

<400> SEQUENCE: 32

```
Lys Leu Ala Lys Leu Ala Lys Lys Leu Ala Lys Leu His Leu Ala His
1               5                   10                  15

Leu Ala His Val Arg Arg Ala Asp Asn Arg Pro Gly
            20                  25
```

<210> SEQ ID NO 33
<211> LENGTH: 27
<212> TYPE: PRT
<213> ORGANISM: Artificial Sequence
<220> FEATURE:
<223> OTHER INFORMATION: KLAK(11)-HLAH(7)-Z13 peptide

<400> SEQUENCE: 33

```
Lys Leu Ala Lys Leu Ala Lys Lys Leu Ala Lys His Leu Ala His Leu
1               5                   10                  15

Ala His Val Arg Arg Ala Asp Asn Arg Pro Gly
            20                  25
```

<210> SEQ ID NO 34
<211> LENGTH: 26
<212> TYPE: PRT
<213> ORGANISM: Artificial Sequence
<220> FEATURE:
<223> OTHER INFORMATION: KLAK(10)-HLAH(7)-Z13 peptide

<400> SEQUENCE: 34

```
Lys Leu Ala Lys Leu Ala Lys Lys Leu Ala His Leu Ala His Leu Ala
1               5                   10                  15

His Val Arg Arg Ala Asp Asn Arg Pro Gly
            20                  25
```

<210> SEQ ID NO 35
<211> LENGTH: 25
<212> TYPE: PRT
<213> ORGANISM: Artificial Sequence
<220> FEATURE:
<223> OTHER INFORMATION: KLAK(9)-HLAH(7)-Z13 peptide

```
<400> SEQUENCE: 35

Lys Leu Ala Lys Leu Ala Lys Lys Leu His Leu Ala His Leu Ala His
1               5                   10                  15

Val Arg Arg Ala Asp Asn Arg Pro Gly
            20                  25

<210> SEQ ID NO 36
<211> LENGTH: 24
<212> TYPE: PRT
<213> ORGANISM: Artificial Sequence
<220> FEATURE:
<223> OTHER INFORMATION: KLAK(8)-HLAH(7)-Z13 peptide

<400> SEQUENCE: 36

Lys Leu Ala Lys Leu Ala Lys Lys His Leu Ala His Leu Ala His Val
1               5                   10                  15

Arg Arg Ala Asp Asn Arg Pro Gly
            20

<210> SEQ ID NO 37
<211> LENGTH: 23
<212> TYPE: PRT
<213> ORGANISM: Artificial Sequence
<220> FEATURE:
<223> OTHER INFORMATION: KLAK(7)-HLAH(7)-Z13 peptide

<400> SEQUENCE: 37

Lys Leu Ala Lys Leu Ala Lys His Leu Ala His Leu Ala His Val Arg
1               5                   10                  15

Arg Ala Asp Asn Arg Pro Gly
            20

<210> SEQ ID NO 38
<211> LENGTH: 23
<212> TYPE: PRT
<213> ORGANISM: Artificial Sequence
<220> FEATURE:
<223> OTHER INFORMATION: KLAK(14D)-Z13 peptide

<400> SEQUENCE: 38

Lys Leu Ala Lys Leu Ala Lys Lys Leu Ala Lys Leu Ala Lys Val Arg
1               5                   10                  15

Arg Ala Asp Asn Arg Pro Gly
            20

<210> SEQ ID NO 39
<211> LENGTH: 14
<212> TYPE: PRT
<213> ORGANISM: Artificial Sequence
<220> FEATURE:
<223> OTHER INFORMATION: KLAK(14)-HLAH(5)-Z13 peptide

<400> SEQUENCE: 39

His Leu Ala His Leu Val Arg Arg Ala Asp Asn Arg Pro Gly
1               5                   10

<210> SEQ ID NO 40
<211> LENGTH: 28
<212> TYPE: PRT
<213> ORGANISM: Artificial Sequence
<220> FEATURE:
<223> OTHER INFORMATION: IF7(RR)-(K+H) peptide

<400> SEQUENCE: 40
```

```
Ile Phe Leu Leu Trp Gln Arg Arg Arg Lys Leu Ala Lys Leu Ala Lys
1               5                   10                  15

Lys Leu Ala Lys Leu Ala Lys His Leu Ala His Leu
            20                  25
```

<210> SEQ ID NO 41
<211> LENGTH: 9
<212> TYPE: PRT
<213> ORGANISM: Artificial Sequence
<220> FEATURE:
<223> OTHER INFORMATION: Z24 peptide

<400> SEQUENCE: 41

```
Met Gln Arg Thr Arg Ala Thr Pro Gly
1               5
```

<210> SEQ ID NO 42
<211> LENGTH: 9
<212> TYPE: PRT
<213> ORGANISM: Artificial Sequence
<220> FEATURE:
<223> OTHER INFORMATION: Z11 peptide

<400> SEQUENCE: 42

```
Val Arg Ser Ser Arg Ser Thr Pro Gln
1               5
```

CYTOCIDAL AGENT

TECHNICAL FIELD

The present invention relates to a peptide drug obtained by selectively inducing apoptosis in a target cell.

Priority is claimed on Japanese Patent Application No. 2017-161556, filed on Aug. 24, 2017, the content of which is incorporated herein by reference.

BACKGROUND ART

Apoptosis means cell death controlled and adjusted as a proliferation inhibition mechanism among cell deaths of multicellular organisms. In multicellular organisms, exclusion of unnecessary cells or harmful cells caused in a generation or reproduction process is performed by inducing apoptosis in the cell. In addition, by inducing apoptosis in a cell which is a cause of a disease and excluding the cell, it is possible to expect improvement in condition of the disease. In this way, substances having activity of inducing apoptosis is used for therapeutic use. For example, by inducing apoptosis in a cancer cell, it can be expected to remit or cure cancer.

In a case where apoptosis induction is used for treatment of a disease, selectivity with respect to a target cell in which apoptosis is induced is very important. In a case where target selectivity is low and apoptosis is induced in a cell other than a target cell, side effects exceed expected therapeutic effects and are not appropriate as a therapeutic drug from a viewpoint of safety. If apoptosis can be induced specifically in a target cell, an effective therapeutic drug in which side effects are sufficiently suppressed is obtained.

Endometriosis is a disease in which endometrial cells proliferate at a site other than an endometrial cavity. In many cases, endometrial cells proliferate in a peritoneum or ovary of pelvis. Representative symptoms include menstrual pain (dysmenorrhea) or infertility, and in a critical case, a patient can experience severe pain or be fainted. In addition, with endometriosis being a matrix, there is a case where cancer occurs. Endometrial cells proliferate under the stimulus of female hormones (estrogen). For this reason, as a therapeutic drug of endometriosis, hormone drugs for inhibiting estrogen secretion, for example, a low-dose pill, a selective agonist (inhibitor against ovarian function and endometrial cell proliferation), and a GnRH agonist (secretion inhibitor of follicle-stimulating hormone) are used. Here, since curative therapy has only an operation of removing the uterus and ovary, it is required to develop a therapeutic drug with which a cure of endometriosis is expected.

For example, Patent Literature 1 discloses a peptide composition including a fusion peptide between a Z13 peptide and an endosome escape peptide specifically binding to cyclic nucleotide-gated channel beta 3 (CNGB3) and a fusion peptide between a Z13 peptide and an apoptosis-inducing peptide. CNGB3 is a molecule that is specifically highly expressed on a cell surface of an endometrial cell (endometrial cell present other than endometriosis) and is not expressed on a peritoneum surface. By incorporating both peptides in an endometrial cell by the Z13 peptide moiety, it is possible to selectively induce apoptosis in an endometrial cell. In one example, a peptide composition including a fusion peptide between a Z13 peptide and an peptide was administered to the peritoneum of a baboon which has developed endometriosis via laparoscopy, selective apoptosis was induced only in a cell of a lesion of endometriosis, and apoptosis was not induced in other adjacent cells (refer to NPL 1).

CITATION LIST

Patent Literature

[PTL 1] United States Patent Application, Publication No. 2016/145308

Non-Patent Literature

[NPL 1] Sugihara, et al., NATURE COMMUNICATIONS, 2014, Volume 5, Article Number 4478.

DISCLOSURE OF INVENTION

Technical Problem

An object of the present invention is to provide a peptide drug that selectively induces apoptosis in a target cell.

Solution to Problem

The present inventors found that, as a result of intensive examination to solve the problem, a peptide composition including a fusion peptide between an endosome escape peptide including a specific peptide sequence, an apoptosis-inducing peptide including a specific peptide sequence, and a Z13 peptide has a high efficiency in terms of higher selectivity and can induce apoptosis in a endometrial cell which expresses CNGB3, compared to the peptide composition including a fusion peptide between a Z13 peptide and an endosome escape peptide and a fusion peptide between a Z13 peptide and an apoptosis-inducing peptide. In addition, the present inventors found that CNGB3 is expressed not only in the endometrium and retina but also in some cancer cells, thereby completing the present invention.

That is, the present invention provides the following cytocidal agent, endometriosis model animal, and the like.

[1] A cytocidal agent having a peptide consisting of an amino acid sequence represented by SEQ ID NO: 1 and a site selectively binding to a target molecule.

[2] The cytocidal agent according to [1], in which the target molecule is a molecule present on a surface of a cell or a tissue.

[3] The cytocidal agent according to [1] or [2], in which the peptide consisting of an amino acid sequence represented by SEQ ID NO: 1 is a peptide exclusively consisting of L-amino acids, a peptide in which, in the amino acid sequence represented by SEQ ID NO: 1, the first to the $14^{th}$ amino acids are D-amino acids, and the $15^{th}$ to $19^{th}$ amino acids are L-amino acids, a peptide in which, in the amino acid sequence represented by SEQ ID NO: 1, the first to $14^{th}$ amino acids are L-amino acids, and the $15^{th}$ to the $19^{th}$ amino acids are D-amino acids, or a peptide exclusively consisting of D-amino acids.

[4] The cytocidal agent according to any one of [1] to [3], in which the site selectively binding to the target molecule is a peptide or a protein, and the peptide consisting of the amino acid sequence represented by SEQ ID NO: 1 and the site selectively binding to the target molecule are directly or indirectly linked to each other.

[5] The cytocidal agent according to any one of [1] to [4], in which the target molecule is CNGB3 or annexin I.

[6] The cytocidal agent according to [1], in which the site selectively binding to the target molecule is a peptide consisting of an amino acid sequence represented by SEQ ID NO: 2, and the site selectively binding to the target molecule is directly or indirectly linked to a downstream of the peptide consisting of the amino acid sequence represented by SEQ ID NO: 1.

[7] The cytocidal agent according to [1], in which the site selectively binding to the target molecule is a peptide consisting of an amino acid sequence represented by SEQ ID NO: 3, and the peptide consisting of the amino acid sequence represented by SEQ ID NO: 1 is directly or indirectly linked to a downstream of the site selectively binding to the target molecule.

[8] The cytocidal agent according to any one of [1] to [7], which is a therapeutic agent of a disease resulting from abnormal proliferation of a cell.

[9] The cytocidal agent according to [8], in which the disease is endometriosis or cancer

[10] An endometriosis model animal, in which a CNGB3-overexpressing cell into which a gene encoding CNGB3 is introduced is transplanted in a peritoneal cavity. [11] A method of determining a disease onset possibility of a disease in which disease-causing cells have expressed CNGB3, including: measuring CNGB3 in an exosome collected from a subject animal, and comparing the obtained measurement value with a pre-set reference value to determine a possibility that the subject animal has developed the disease.

[12] The method of determining a disease onset possibility according to [11], wherein determining that the subject animal has a high possibility of developing the disease if the measurement value exceeds the reference value.

[13] The method of determining a disease onset possibility according to [11] or [12], wherein the exosome is isolated from blood collected from the subject animal.

[14] The method of determining a disease onset possibility according to any one of [11] to [13], wherein measuring CNGB3 by using a peptide consisting of an amino acid sequence represented by SEQ ID NO: 2.

[15] The method of determining a disease onset possibility according to any one of [11] to [14], in which the subject animal is a human.

[16] The method of determining a disease onset possibility according to any one of [11] to [15], in which the disease is endometriosis or cancer. [17] A biomarker which includes an amount of CNGB3 in an exosome and is used for determining presence or absence of disease onset of endometriosis or cancer.

Advantageous Effects of Invention

The cytocidal agent according to the present invention can very efficiently induce apoptosis in a target cell. For this reason, the cytocidal agent is particularly effective as a therapeutic agent of a disease resulting from abnormal proliferation of a cell of endometriosis or cancer. In addition, the endometriosis model animal according to the present invention is useful for drug efficacy tests on therapeutic agent candidate substances of endometriosis. In addition, by the disease onset evaluation method and the biomarker according to the present invention, it is possible to conveniently and efficiently evaluate a disease onset possibility of a disease that specifically expresses CNGB3 such as endometriosis and cancer.

BESTMODE FOR CARRYING OUT THE INVENTION

<Cytocidal Agent>

Figure 1:
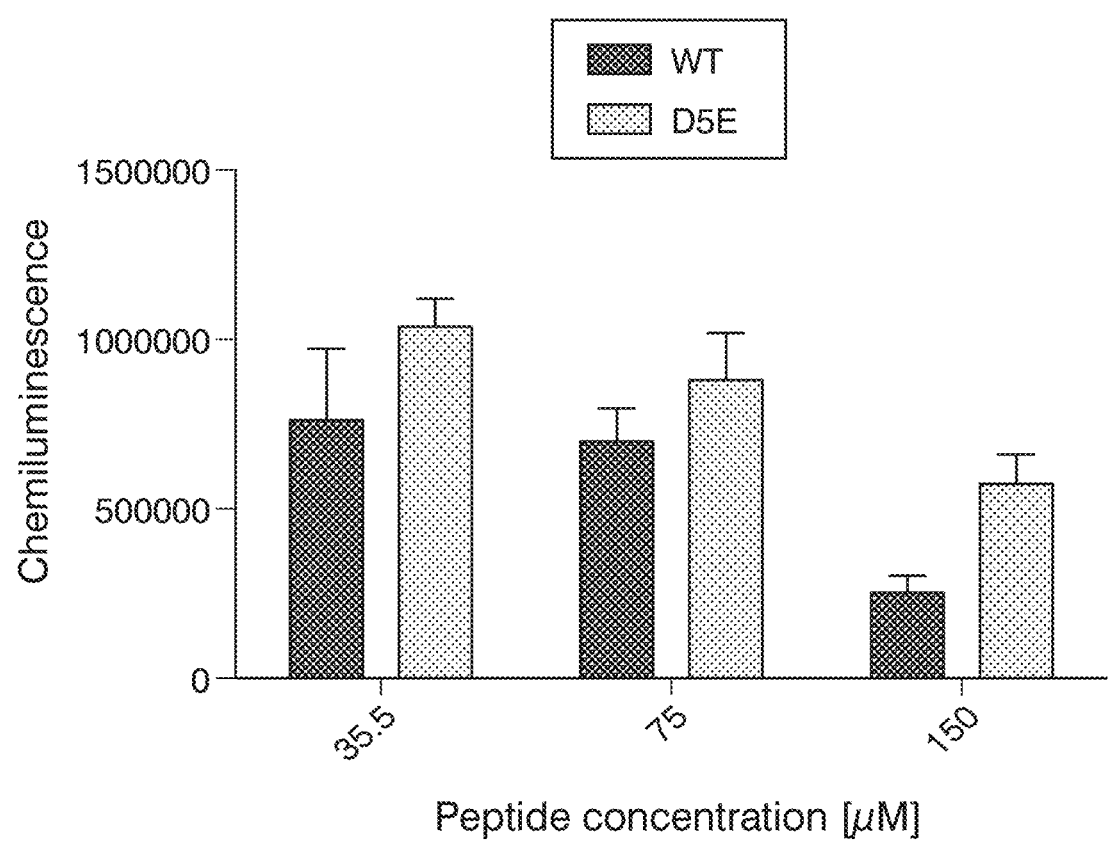
FIG. 1 is a view illustrating a measurement result of emission intensity (RIX) of a reaction solution treated with each peptide in Reference Example 1.

The cytocidal agent according to the present invention has a peptide consisting of an amino acid sequence (KLAK-LAKKLAKLAKHLAHL) represented by SEQ ID NO: 1 (hereinafter, referred to as "effector peptide") and a site selectively binding to a target molecule. The effector peptide is a peptide in which a peptide having an apoptosis-inducing activity and a peptide having an endosome escape activity are linked in tandem. The cytocidal agent according to the present invention binds to a target molecule through a site selectively binding to the target molecule and is taken into the target cell by endocytosis. Subsequently, as a result of destructing an endosome membrane by the action of the peptide site having endosome escape activity, the cytocidal agent included in endosome taken into the target cell is released in cytoplasm of the target cell. The cytocidal agent released in cytoplasm induces apoptosis of the target cell by interfering with mitochondrial membrane by the action of the peptide site having apoptosis-inducing activity.

The cytocidal agent according to the present invention includes all of a peptide moiety having apoptosis-inducing activity, a peptide moiety having endosome escape activity, and a site selectively binding to a target molecule in a molecule. For this reason, it is possible to very efficiently induce apoptosis in a target cell, compared to a peptide composition each independently including a peptide in which a peptide selectively binding to a target molecule is linked to a peptide having apoptosis-inducing activity and a peptide in which a peptide selectively binding to a target molecule is linked to a peptide having endosome escape activity.

In the present invention and the present specification, the "target cell" is a subject cell in which apoptosis is induced. The "target molecule" is a molecule present on a surface of a subject cell in which apoptosis is induced or a tissue surface on which the cell is present, and is a molecule to which the cytocidal agent according to the present invention selectively binds.

As disclosed in Patent Literature 1, a peptide (hereinafter, referred to as "KLAK peptide") consisting of an amino acid sequence (hereinafter, referred to as "KLAK sequence") consisting of 4 amino acid repeats of KLAK has an action (apoptosis-inducing activity) of inducing apoptosis by interfering with mitochondrial membrane. In addition, a peptide (hereinafter, referred to as "HLAH peptide") consisting of an amino acid sequence (hereinafter, referred to as "HLAH sequence") consisting of 4 amino acid repeats of HLAH has an action (endosome escape activity) of destructing the endosome membrane. The peptide in which the KLAK peptide is linked to the HLAH peptide has endosome escape activity and apoptosis-inducing activity. However, the intensity of the respective activities is affected by the length of amino acids in each peptide and the order of the linkage. Both of the peptide in which the HLAH peptide is linked to a downstream (C-terminal) of the KLAK peptide and the peptide in which the KLAK peptide is linked to a downstream (C-terminal) of the HLAH peptide has endosome escape activity and apoptosis-inducing activity, but the peptide in which the HLAH peptide is linked to a downstream (C-terminal) of the KLAK peptide has high apoptosis-inducing activity.

The effector peptide consisting of an amino acid sequence represented by SEQ ID NO: 1 is a peptide in which an HLAH sequence consisting of 5 amino acids is linked to a downstream of the KLAK sequence consisting of 14 amino acids. That is, in the amino acid sequence of SEQ ID NO: 1, the first to the $14^{th}$ amino acids are sites having apoptosis-inducing activity and the $15^{th}$ to the $19^{th}$ amino acids are sites having endosome escape activity. In order to obtain the highest apoptosis-inducing activity in a case of being taken into the target cell, the effector peptide is a peptide in which the length of the KLAK sequence, the length of the FILAH sequence, and the order of linkage of the KLAK sequence and the FILAH sequence are optimized. Since the cytocidal agent has the effector peptide, the cytocidal agent according to the present invention has very high apoptosis-inducing activity.

The effector peptide included in the cytocidal agent according to the present invention is not particularly limited as long the peptide is a peptide consisting of an amino acid sequence represented by SEQ ID NO: 1, may be a peptide consisting of a L-amino acid, may be a peptide consisting of a D-amino acid, or may be a peptide consisting of a L-amino acid and a D-amino acid. Since stability is high in the endosome and higher apoptosis-inducing activity is obtained, the effector peptide is preferably a peptide consisting of at least some D-amino acids, at least one of the KLAK sequence (in the amino acid sequence represented by SEQ ID NO: 1, the first to the $14^{th}$ amino acids) and the HLAH sequence (in the amino acid sequence represented by SEQ ID NO: 1, the $15^{th}$ to the $19^{th}$ amino acids) is more preferably a peptide consisting of a D-amino acid, and all thereof is particularly preferably a peptide consisting of a D-amino acid.

In the cytocidal agent according to the present invention, the effector peptide including a site selectively binding to a target molecule and an amino acid sequence represented by SEQ ID NO: 1 may directly bind, or may indirectly bind via a linker. The linker is not particularly limited, and examples thereof include a peptide of 1 to 20 amino acids, a sugar chain, polyethylene glycol, polyolefin, and the like. Since synthesis is relatively easy, as the cytocidal agent according to the present invention, those in which a site selectively binding to a target molecule is a peptide or protein, and which binds to the effector peptide directly or via a peptide of 1 to 20 amino acids are preferable. In addition, in the cytocidal agent according to the present invention, the site selectively binding to a target molecule may be linked to an N-terminal side of the effector peptide consisting of an amino acid sequence represented by SEQ ID NO: 1, or may be linked to a C-terminal side as long as binding properties to the target molecule is not hindered.

The site selectively binding to a target molecule in the cytocidal agent according to the present invention is not particularly limited, and is determined according to the target molecule. The site may be a peptide or protein, may be an oligo nucleotide or nucleic acid, may be a sugar chain, may be a lipid, or may be a low-molecular compound.

The target molecule to which the cytocidal agent according to the present invention selectively binds is not particularly limited as long as the target molecule is a molecule present on a surface of a target cell or tissue in which apoptosis is induced, and may be a protein, may be a sugar chain, or may be a lipid.

Selectivity of the cytocidal agent according to the present invention becomes high, and thus side effects are decreased in a case of being used as a therapeutic agent of various diseases. From this, as the target molecule to which the cytocidal agent according to the present invention selectively binds, a molecule, in which an expression amount on a surface of a target cell or a tissue surface including the target cell is prominently large compared to the expression amount in many other cells or tissues, is preferable, and a molecule, which is specifically expressed on the surface of the target cell or the tissue surface including the target cell, is more preferable.

For example, CNGB3 is a membrane protein highly expressed only in the endometrium and retina in normal tissues. Local existence of CNGB3 in normal tissues is very biased, and it is only shown that moderate expression is confirmed in pineal bodies and weak expression is confirmed in bone marrow, choroid plexus, oviduct, eyes, ovaries, and testes. For this reason, the cytocidal agent having CNGB3 as a target molecule in the cytocidal agent according to the present invention is a cytocidal agent capable of specifically inducing apoptosis in the endometrium or retina, and is useful as a therapeutic agent for diseases of the endometrium or retina. In particular, since apoptosis is not induced in normal cells in the peritoneal cavity or pelvis, and apoptosis can be selectively induced in endometrial cells, it is very appropriate as a therapeutic agent for endometriosis.

In addition, CNGB3 is relatively strongly expressed in various cancer cells as well. For this reason, the cytocidal agent having CNGB3 as a target molecule in the cytocidal agent according to the present invention has high selectivity with respect to a cancer cell that expresses CNGB3 and is useful as an anti-cancer drug in which side effects are suppressed. Examples of cancers that expresses CNGB3 include uterine cancer, cervical cancer, pelvic cavity cancer, ovarian cancer, breast cancer, peritoneal wall cancer, omentum majus tumor, esophagus cancer, stomach cancer, small intestinal cancer, colon cancer, rectal cancer, appendix cancer, gall bladder cancer, pancreatic cancer, liver cancer, splenic cancer, kidney cancer, tongue cancer, pharynx cancer, nasal cancer, parotid gland cancer, thyroid cancer, malignant lymphoma, bone tumor, skin cancer, lung cancer, mediastinal cancer, testis cancer, prostate cancer, bladder cancer, brain tumor, and the like. Even cancer cells derived from the same kinds of tissues include both cancer cells which express CNGB and cancer cells which do not express CNGB. For this reason, in a case where the cytocidal agent having CNGB3 as a target molecule in the cytocidal agent according to the present invention is used as an anti-cancer drug, it is preferable to check in advance by biopsy and the like that a target cancer cell is a cell which expresses CNGB3.

In a case where CNGB3 is used as a target molecule, examples of the site selectively binding to the target molecule include a peptide consisting of an amino acid sequence represented by SEQ ID NO: 2 (VRRAXNXPG; X represents an optional amino acid present naturally), a peptide consisting of an amino acid sequence obtained by partially modifying the amino acid sequence represented by SEQ ID NO: 2 (hereinafter, the peptide is referred to as "CNGB3-binding peptide"), and the like (Patent Literature 1). Examples of the peptide consisting of an amino acid sequence obtained by partially modifying the amino acid sequence represented by SEQ ID NO: 2 include a peptide in which 1, 2, or 3 amino acids of the amino acid sequence represented by SEQ ID NO: 2 are deleted, replaced, or added, and maintains binding properties to CNGB3; a peptide which has at least 75% or more, preferably 85% or more, and more preferably 90% or more sequence identity to the amino acid sequence represented by SEQ ID NO: 2 and maintains binding properties to CNGB3; and the like. Specific examples of the CNGB3-binding peptide include a peptide consisting of an amino acid sequence represented by SEQ ID NO: 3 (VRRADNRPG) (hereinafter, referred to as "Z13 peptide"), a peptide consisting of an amino acid sequence represented by SEQ ID NO: 4 (VRRAENRPG), a peptide consisting of an amino acid sequence represented by SEQ ID NO: 5 (VRRANNNLPG), a peptide consisting of an amino acid sequence represented by SEQ ID NO: 6 (VRRANNRPG), and the like.

From a viewpoint of stronger apoptosis-inducing activity in a cell which expresses CNGB3, as the cytocidal agent having CNGB3 as a target molecule, a peptide in which the Z13 peptide and the effector peptide are linked directly or indirectly via a linker is preferable, a peptide in which the Z13 peptide and the effector peptide are linked directly or via a peptide consisting of 1 to 20 amino acids is more preferable, a peptide in which the Z13 peptide is linked to the C-terminal of the effector peptide directly or via 1 to 20 amino acids are further more preferable, a peptide in which the C-terminal of the effector peptide is directly linked to the N-terminal of the Z13 peptide (SEQ ID NO: 26: KLAK-LAKKLAKLAKHLAHLVRRADNRPG) is even further more preferable, and a peptide in which the C-terminal of the effector peptide exclusively consisting of D-amino acids is directly linked to the N-terminal of the Z13 peptide exclusively consisting of all L-amino acids is particularly preferable.

In addition, annexin I is a membrane protein which is expressed in cytoplasm in normal vascular endothelial cells, but is specifically expressed on the blood stream side of the vascular endothelial cells of new blood vessels (new tumor blood vessel) in malignant tumor tissues. A molecule selectively binding to the annexin I administered into a living body is taken into the vascular endothelial cells of new tumor blood vessels via a bond to annexin I expressed on the blood stream side of the new tumor blood vessels in the malignant tumor tissues. The molecule taken into the vascular endothelial cells are transported from the apical side to the basal side by vesicle transport and discharged to interstitial cells. The discharged molecule is diffused in interstitial cells and taken into tumor cells. For this reason, a cytocidal agent having annexin I as a target molecule in the cytocidal agent according to the present invention is a cytocidal agent capable of inducing apoptosis in a cancer cell, and is useful as an anti-cancer drug. The cytocidal agent having annexin I as a target molecule is specifically taken into the vascular endothelial cells of new tumor blood vessels, and in the vesicle transport process in the vascular endothelial cells or in the vesicle transport process in the taken tumor cells, a membrane of endosome is destructed by a function of HLAH peptide moiety and released into cytoplasm. After that, by a function of KLAK peptide moiety, cells into which the cytocidal agent is taken are killed. In a case where a cytocidal agent having annexin I as a target molecule is used as an anti-cancer drug, cancers which are therapeutic subjects are not particularly limited, and can be used for the same cancer as those exemplified described above.

In a case of having annexin I as a target molecule, examples of a site selectively binding to a target molecule include a peptide consisting of an amino acid sequence represented by SEQ ID NO: 7 (IFLLWQR) (hereinafter, referred to as "IF7 peptide") and a peptide consisting of an amino acid sequence in which a moiety of the amino acid sequence represented by SEQ ID NO: 7 is modified (hereinafter, the peptide is referred to as "annexin I-binding peptide"). Examples of the peptide consisting of an amino acid sequence in which a moiety of the amino acid sequence represented by SEQ ID NO: 7 is modified include a peptide in which one, two, or three amino acids of the amino acid sequence represented by SEQ ID NO: 7 are deleted, substituted, or added and which maintains binding performance to annexin I or a peptide which has at least 70% or more, and preferably 85% or more sequence identity with the amino acid sequence represented by SEQ ID NO: 7 and maintains binding performance to annexin I.

From a viewpoint of having stronger apoptosis-inducing activity to cancer cells, the cytocidal agent having annexin I as a target molecule is preferably a cytocidal agent in which an IF7 peptide and the effector peptide are linked directly or indirectly via a linker, more preferably a peptide in which the IF7 peptide and the effector peptide are linked directly or via a peptide consisting of 1 to 20 amino acids, even more preferably a peptide in which the effector peptide is linked to a C-terminal of the IF7 peptide directly or via a peptide consisting of 1 to 20 amino acids, still even more preferably a peptide in which the effector peptide is linked to a C-terminal of the IF7 peptide via a peptide consisting of 1 to 5 amino acids, and particularly preferably a peptide in which a C-terminal of the IF7 peptide exclusively consisting of L-amino acids is linked to a N-terminal of the effector peptide exclusively consisting of D-amino acids via a peptide consisting of 1 to 5 L-amino acids. Examples of the peptide in which the C-terminal of the IF7 peptide is linked to the N-terminal of the effector peptide via a peptide consisting of 1 to 5 amino acids include an amino acid sequence (IFLLWQRRRKLAKLAKKLAKLAKHLAHL) represented by SEQ ID NO: 40.

In a case where the cytocidal agent according to the present invention is used as a therapeutic drug, the administration path is not particularly limited, and appropriately determined depending on the target cell and tissues including thereof. Examples of the administration path of the cytocidal agent according to the present invention include oral administration, intravenous administration, intraperitoneal administration, enema administration, and the like.

The cytocidal agent according to the present invention can be formulated as an oral solid agent such as a powder, a granule, a capsule, a tablet, and a chewable agent, an oral liquid agent such as a solution agent and a syrup agent, an injection, an enema agent, a spray agent, a patch, and an ointment by a general method.

The cytocidal agent according to the present invention is formulated by being mixed with an excipient, a binding agent, a lubricant, a disintegrating agent, a fluidizing agent, a solvent, a solubilizing agent, a buffer, a suspending agent, an emulsifier, an isotonizing agent, a stabilizer, an antiseptic agent, an anti-oxidant, a flavoring agent, a coloring agent, and the like, depending on the formulation necessity.

Examples of the excipient include saccharides such as lactose, glucose, and D-mannitol, celluloses such as starch and crystalline cellulose, sugar alcohols such as erythritol, sorbitol, and xylitol, dicalcium phosphate, calcium carbonate, and kaoline. Examples of the binding agent include pregelatinized starch, gelatin, Arabic rubber, methyl cellulose, carboxy methyl cellulose, sodium carboxy methyl cellulose, crystalline cellulose, D-mannitol, trehalose, hydroxy propyl cellulose, hydroxy propyl methyl cellulose, polyvinyl pyrrolidone, polyvinyl alcohol, and the like. Examples of the lubricant include stearic acid, calcium stearate, talc, sucrose fatty acid ester, polyethylene glycol, and the like. Examples of the disintegrating agent include crosslinking polyvinyl pyrrolidone (crospovidone), low substitution degree hydroxy propyl cellulose, starch, alginic acid, sodium alginate, and the like. Examples of the fluidizing agent include silicic acid, silicic anhydride, aluminum silicate, calcium silicate, a magnesium metasilicate aluminate compound, an aluminum oxide, aluminum hydroxide, a magnesium oxide, a magnesium hydroxide, and the like. Examples of the solvent include purified water, a physiological saline solution, and the like. Examples of the solubilizing agent include dextran, polyvinyl pyrrolidone, sodium benzoate, ethylene diamine, salicylate amide, nicotinic acid amide, a polyoxy ethylene hydrogenated castor oil derivative, and the like. Examples of the buffer include sodium citrate hydrate, sodium acetate hydrate, sodium hydrogen carbonate, trometamol, boric acid, borax, dibasic sodium phosphate hydrate, sodium dihydrogen phosphate, and the like. Examples of the suspending agent or the emulsifier include sodium lauryl sulfate, Arabic rubber, gelatin, lecithin, glyceryl monostearate, polyvinyl alcohol, polyvinyl pyrrolidone, celluloses such as sodium carboxy methyl cellulose, polyoxy ethylene hydrogenated castor oil, and the like. Examples of the isotonizing agent include saccharides such as lactose, glucose, and D-mannitol, sodium chloride, potassium chloride, glycerin, propylene glycol, polyethylene glycol, urea, and the like. Examples of the stabilizer include polyethylene glycol, sodium dextran sulfate, sodium sulfite, and the like. Examples of the antiseptic agent include para-hydroxybenzoic esters, chlorobutanol, benzyl alcohol, phenethyl alcohol, chlorocresol, dehydroacetic acid, sorbic acid, and the like. Examples of the anti-oxidant include sulfite, ascorbic acid, and the like. Examples of the flavoring agent include sweeteners generally used in the field of the therapeutic drug and the food, aromatic chemical, and the like. Examples of the coloring agent include coloring materials generally used in the field of the therapeutic drug and the food.

The cytocidal agent according to the present invention may be used as it s, and can be also used as a therapeutic composition including other components. Examples of the other components included in the therapeutic composition include the excipient, the binding agent, the lubricant, the disintegrating agent, the fluidizing agent, the solvent, the solubilizing agent, the buffer, the suspending agent, the emulsifier, the isotonizing agent, the stabilizer, the antiseptic agent, the anti-oxidant, the flavoring agent, the coloring agent, and the like. In addition, the therapeutic composition may contain other effective components than the cytocidal agent according to the present invention.

The cytocidal agent according to the present invention is preferably administered to mammals, more preferably administered to humans or livestock such as mouse, rat, rabbit, guinea pig, hamster, monkey, sheep, horse, cattle, pig, donkey, dog, and cat, and further more preferably administered to humans.

<Endometriosis Model Animal>

Endometriosis cells express CNGB3. In addition, in many endometriosis, the endometriosis cells proliferate in the peritoneal cavity. For this reason, it is possible to set the animal in which CNGB3-overexpressing cells are transplanted in the peritoneal cavity as an endometriosis model animal.

Overexpressed CNGB3 is not particularly limited as long as the CNGB3 is a protein exhibiting the same function as that of a wild type human CNGB3 (Gene ID: 54714 of NCBI) expressed in the endometriosis cells. For example, the CNGB3 may be a human CNGB3, may be a homolog protein of human CNGB3 derived from an animal other than a human, may be a modified body of a human CNGB3 or the homolog, or may be a protein having the same function as that of a human CNGB3.

Examples of the modified body include a protein consisting of an amino acid sequence in which one or a plurality of amino acids of an amino acid sequence of the human CNGB3 or the homolog are deleted, substituted, or added and having the function as CNGB3. The number of amino acids to be deleted and the like is preferably 1 to 50, more preferably 1 to 30, further more preferably 1 to 20, and even more preferably 1 to 10. Examples of amino acids added to the N-terminal or C-terminal of the human CNGB3 or the homolog include a tag peptide such as His tag, Myc tag, and Flag tag. In addition, examples of the modified body include a protein that includes an amino acid sequence having 70% or more sequence identity, preferably 80% or more sequence identity, further more preferably 85% or more sequence identity, even more preferably 90% or more sequence identity, and even further more preferably 95% or more sequence identity with the amino acid sequence of the human CNGB3 or the homolog and has a function as CNGB3.

In the present invention and the specification of the present application, "amino acids are deleted in protein" means that some amino acids constituting protein are lost (removed).

In the present invention and the specification of the present application, "amino acids in protein are substituted" means that amino acids constituting protein are changed into other amino acids.

In the present invention and the specification of the present application, "amino acids in protein are added" means that new amino acids are inserted in protein.

In order to prepare CNGB3-overexpressing cells, a cell (host cell) into which genes (CNGB3 genes) encoding CNGB3 are introduced may not be particularly limited, may be a uterine endothelial cell, may be a primary culture cell of a cell other than the uterine endothelial cell collected from animal tissues, or may be a culture cell strain. In addition, the host cell into which CNGB3 genes are introduced may be a human-derived cell, or may be a cell derived from an animal other than a human.

The CNGB3-overexpressing cell is obtained by introducing CNGB3 genes in a host cell in an expressible state. Specifically, an expression vector into which an expression cassette including a combination of DNA required for expressing CNGB3 is incorporated is introduced into the host cell. The expression cassette includes a gene encoding the expressed protein and a promoter controlling expression of the gene. The expression cassette may further contain any one or more of terminators, a 5'-untranslated region, and a 3'-untranslated region. A preferable expression cassette is an expression cassette including all of a gene sequence encoding a protein, a promoter, a terminator, a 5'-untranslated region, and a 3'-untranslated region. The CNGB3 gene introduced into the host cell may be any gene as long as the gene include a base sequence encoding CNGB3 consisting of a target amino acid sequence, or may be modified depending on codon frequency of the host cell.

The promoter and the terminator may be any ones as long as the promoter and the terminator function in the host cell. The promoter and the terminator that function in the host cell may be originally included in the host cell, or may not be originally included in the host cell.

As a vector for preparing an expression vector into which an expression cassette of a CNGB3 gene is incorporated, it is possible to use an optional vector generally used in introduction to the host cell. The vector may be a circular plasmid vector, may be a straight-chain vector, or may be a virus vector such as adeno virus. It is possible to prepare an expression vector also by incorporating a CNGB3 gene into a cloning site of a commercially available mammal cell expression vector.

The CNGB3-overexpressing cell may be a transformant in which the expression cassette of the CNGB3 gene is held as an extrachromosomal gene in the cell of the host cell or a transformant incorporated in the chromosome of the host cell. In addition, as a transformation method of introducing an expression vector into a mammal cell serving as a host, it is possible to appropriately select a method among known transformation methods such as lipofection method, a calcium phosphate deposition method, a lithium acetate method, and an electroporation method and perform thereof. The obtained CNGB3-overexpressing cell can be cultured under the same condition as that of the mammal cell serving as a host.

The kind of the organism of non-human animals in which CNGB3-overexpressing cell is transplanted in a peritoneal cavity is not particularly limited. As the endometriosis model animal according to the present invention, livestock such as mouse, rat, rabbit, guinea pig, hamster, monkey, sheep, horse, cattle, pig, donkey, dog, and cat or test animals are preferable, for example. Transplantation of the CNGB3-overexpressing cell into a peritoneal cavity can be generally performed.

<Biomarker>

Exosome includes biomolecules expressed in cell membranes of original cells from which the exosome was released. As described above, the large amount of CNGB3 is expressed in the cell membranes of the endometrial cell, and the exosome released from the endometrial cell includes CNGB3. Similarly, CNGB3 is also expressed in various cancer cells, and the exosome released from cancer cells includes CNGB3. For this reason, the amount of CNGB3 in the exosome is useful as a biomarker of endometriosis or cancer.

<Method of Determining Disease Onset Possibility>

A method of determining a disease onset possibility according to the present invention (hereinafter, referred to as "evaluation method according to present invention") is a method of determining a disease onset possibility of a disease in which CNGB3 is expressed, using the CNGB3 in exosomes as a biomarker. In an animal body in which disease-causing cells have expressed CNGB3 to develop a disease (hereinafter, referred to as "CNGB3 high expression disease"), a large amount of exosomes including a large amount of CNGB3 is secreted from the disease-causing cells. On the other hand, since CNGB3 is expressed only in limited tissues in normal cells, exosomes including a large amount of CNGB3 are very few in the animal body not developing CNGB3 high expression disease. For this reason, based on the amount of CNGB3 in the exosome, it is possible to identify the patient group and the non-patient group of the CNGB3 high expression disease. In the evaluation method according to the present invention, a possibility that the subject animal has developed CNGB3 high expression diseases is evaluated by measuring CNGB3 in the exosome collected from the subject animal, and comparing the obtained measurement value with a pre-set reference value.

As the CNGB3 high expression diseases, endometriosis or cancer in which CNGB3 is expressed is exemplified. In addition, the subject animal which is a subject evaluated by the evaluation method according to the present invention may be a human, or may be a non-human animal. The kind of organism of the non-human animals is not particularly limited, and examples thereof include livestock such as mouse, rat, rabbit, guinea pig, hamster, monkey, sheep, horse, cattle, pig, donkey, dog, and cat or test animals. As the subject animal which is a subject evaluated by the evaluation method according to the present invention, humans, livestock, and test animals are preferable, and humans are more preferable.

Specifically, in a case where the measurement value of CNGB3 in the exosome is more than the pre-set reference value, it is evaluated that the subject animal from which the exosome is collected has a high possibility of developing a CNGB3 high expression disease. The reference value is a reference value for identifying patients and non-patients of the CNGB3 high expression disease.

The reference value can be experimentally obtained as a threshold capable of measuring the amount of CNGB3 in the exosome of the patient group and the non-patient group of a CNGB3 high expression disease and distinguishing the both groups. A method of determining a reference value of the amount of CNGB3 in the exosome in the present invention is not particularly limited, and, for example, is obtained by a general statistical method.

As an example of a method of obtaining a reference value, for example, an exosome of a patient diagnosed as a patient with a target CNGB3 high expression disease is collected by other methods such as a generally performed pathological examination, and the amount of the CNGB3 is measured. After performing measurement on a plurality of patients, it is possible to calculate the amount of CNGB3 in the exosome thereof by the average value or median value and to set a numerical value including thereof as a reference value.

In addition, it is possible to perform measurement on the amount of CNGB3 in the exosome with respect to a plurality of CNGB3 high expression patients and a plurality of CNGB3 high expression non-patients, to calculate both of the amount of CNGB3 in the exosome of the CNGB3 high expression patient group and the CNGB3 high expression non-patient group and variation by an average value or median value, to obtain a threshold in which both numerical values are distinguished by considering variations, and to set thereof as a reference value.

In the CNGB3 high expression disease to be evaluated, in a case where CNGB3 is specifically expressed in the disease-causing cells, the reference value can be set as a detection limit value of CNGB3. In a case where CNGB3 is detected from the exosome collected from the subject animal, it can be evaluated that the subject animal has a high possibility of developing the CNGB3 high expression disease, and in a case where the CNGB3 is not detected, it can be evaluated that the subject animal has a high possibility of not developing the CNGB3 high expression disease.

The measurement method of the amount of CNGB3 in the exosome collected from the subject animal is not particularly limited, and measurement can be carried out by various methods generally used when quantitatively or semi-quantitatively measuring expression of the protein. Examples of the method include methods using immune reaction such as an ELISA method, immunohistochemistry, and a Western blotting method. In addition, the amount of CNGB3 in the exosome collected from the subject animal may be obtained as an amount of exosome including CNGB3. The CNGB3 is mainly present on a lipid double membrane surface of the exosome. For this reason, it is possible to measure the amount of CNGB3 in the exosome also by applying various methods of measuring exosome having a specific surface molecule. Examples of devices measuring the exosome having a specific surface molecule include exosome measurement systems such as "Exo Counter" (manufactured by JVC Kenwood Corporation), "dNano" (manufactured by Meiwafosis Co., Ltd.), "Nano Sight" (manufactured by Quantum Design Japan), and "SP6800" (Sony Corporation).

In a measurement method using immune reaction, any anti-CNGB3 antibody may be used. In addition, instead of the anti-CNGB3 antibody, it is possible to use a molecule binding to CNGB3. As the molecule, any of peptide, protein, nucleic acid, low molecule, and the like may be used. In addition, the molecule is preferably a labeled product (one in which a labeling substance directly or indirectly binds to a site binding to CNGB3). The labeling substance is not particularly limited, and, for example, may be a low molecule such as biotin, may be a fluorescent substance, may be an enzyme, or may be a tag peptide such as His tag, Myc tag, and Flag tag.

For example, the peptide binding to CNGB3 is preferably the above-described CNGB3-binding peptide or the labeled product, and is particularly preferably a Z13 peptide or the labeled product. In addition, it is also possible to use a peptide bindable to CNGB3 such as a peptide consisting of an amino acid sequence represented by SEQ ID NO: 41 (MQRTRATPG) (hereinafter, referred to as "Z24 peptide") and a peptide consisting of an amino acid sequence represented by SEQ ID NO: 42 (VRSSRSTPQ) (hereinafter, referred to as "Z11 peptide") (for either thereof, refer to NPL 1). As the peptide binding to CNGB3, a peptide in which all of the peptide moiety consists of L-amino acids may be used, and it is also possible to use a peptide consisting of D-amino acids. For example, it is possible to use a biotinylated Z13 peptide, and a set of avidin and streptovine labeled with enzyme and fluorescence.

The exosome used in measurement of the amount of CNGB3 may be an exosome collected from a subject animal, or may be a biological sample itself collected from the subject animal, but is preferably an exosome purified from the biological sample. Separation of the exosome from the biological sample can be performed by using a kit for commercially available exosome separation, for example.

The biological sample including an exosome is not particularly limited, but may be blood, plasma, serum, tear, saliva, peritoneal fluid, urine, and the like, or may be tissue pieces collected from a mucous membrane such as uterine mucosa and digestive tract mucous membrane or tissues such as liver, stomach, small intestine, and large intestine. Among these, blood, plasma, and serum are widely used as clinical specimens and can be relatively minimally invasively collected. For this reason, as the exosome used in measurement of the amount of CNGB3 in the evaluation method according to the present invention, an exosome isolated from blood collected from a specimen animal, particularly plasma or serum, is preferable. Since the evaluation method according to the present invention can be carried out using the exosome isolated from serum and the like as a sample, the evaluation method according to the present invention is also effective in fast screening of CNGB3 high expression disease such as health diagnosis.

The evaluation method according to the present invention can be used in evaluation of therapeutic effects in treatment of the CNGB3 high expression disease. For example, the evaluation method according to the present invention is performed on a patient with the CNGB3 high expression disease before starting and after completion of treatment of the CNGB3 high expression disease. In a case where the CNGB3 high expression disease-causing cells were decreased, or the physiological activity was lowered in a patient's body by the treatment, in the patient's body, the amount of the exosome secreted from the CNGB3 high expression disease-causing cells is lowered. For this reason, in a case where the amount of CNGB3 in the exosome is significantly decreased after treatment compared to before treatment, it can be evaluated that the therapeutic effect is obtained by the treatment. In addition, it can be evaluated that the greater the percentage of decrease in the amount of CNGB3 in the exosome gets, the higher the therapeutic effect becomes. It is possible to monitor the therapeutic effect by performing the evaluation method according to the present invention over time even during the treatment period, in addition to before starting and after completion of treatment of the CNGB3 high expression disease.

In addition, by performing the evaluation method according to the present invention on an animal affected by the CNGB3 high expression disease at least once over time, it is possible to monitor presence or absence of disease onset of the CNGB3 high expression disease of the affected animal. For example, in a case where the CNGB3 high expression disease is a disease which has a high recurrence risk even in a cured case such as cancer or endometriosis, by performing the evaluation method according to the present invention on a patient with the CNGB3 high expression disease over time, it is possible to monitor presence or absence of recurrence.

EXAMPLES

Subsequently, the present invention will be further explained in detail using examples. The present invention is not limited to the following examples.

<Endometriosis Model Cell (A431-CNGB3-myc Cell)>

A transformed cell (A431-CNGB3-myc cell) obtained by introducing a gene encoding human CNGB3, in which an myc tag was fused in a C-terminal, into an A431 cell (human epithelial-like cell cancer-derived cell strain) and forcibly expressing thereof was prepared as an endometriosis model cell.

Culturing of the A431-CNGB3-myc cell was performed at 37° C. in a 5 volume % carbon dioxide environment using a medium in which 10% of inactivated FBS (bovine fetal serum, manufactured by Corning Corporation) and 1% of penicillin-streptomycin (manufactured by Invitrogen Corporation) were contained in a DMEM High Glucose medium (manufactured by GIBCO Corporation), as a culture medium. Passage was performed every two or three days.

<Endometriosis Model Mouse>

A431-CNGB3-myc cells were transplanted to a peritoneal cavity of an immunodeficient mouse NOD/ShiJic-scid Jcl strain, supplied by CLEA Japan, Inc.) to prepare an endometriosis model mouse.

Specifically, after thawing frozen-stored A431-CNGB3-myc cells, a cell solution prepared by adding a culture medium to cells passaged twice using a 10-cm dish (manufactured by Thermo Fisher Scientific Co., Ltd., Lot No. F3BAXQ103) so as to be $1 \times 10^7$ cells/0.5 mL/body was used as an administration solution. The administration solution was intraperitoneally administered to a 7-week-old female immunodeficient mouse as soon as possible after preparation to transplant the A431-CNGB3-myc cells.

For the mouse, 5 to 10 mice/cage in a polycarbonate cage (W×D×H=270×440×187 (mm)) were bred in an environment of 19.8° C. to 27.1° C., humidity of 32% to 75%, and 12 hours of light. Feed (sterilized CRF-1 (solid type), manufactured by Oriental Yeast Co., Ltd.) and drinking water (sterile tap water) were freely ingested.

Model preparation was confirmed by observation and collection of a peritoneal tumor. One to three weeks after A431-CNGB3-myc cell transplantation, autopsy was performed on each two mice a week to visually check whether a tumor (granular shape of about 1 mm) was observed in the peritoneum and photographed. Thereafter, the peritoneum was collected, and 4 locations (each on the left and right sides of the abdomen and back) were cut out, immersed and fixed in 10% neutral butter formalin, respectively, and refrigerated. The peritoneum after formalin fixation was subjected to immunohistochemical staining using an anti-c-myc antibody to examine the status of dissemination.

As a result of visual checking of the mouse after A431-CNGB3-myc cell transplantation, in the first test, although a tumor was visually confirmed 1 week after transplantation, no peritoneal dissemination was observed, but two or three weeks after transplantation, a tumor and peritoneal dissemination were visually confirmed. In the second test, peritoneal dissemination was visually confirmed even one week after transplantation. In addition, as a result of c-myc staining of the peritoneal tissue fragment of the mouse after transplantation, it was confirmed that one week after the transplantation, peritoneal dissemination was already proceeded.

Reference Example 1

In a peptide in which a KLAK peptide, an HLAH peptide, and a CNGB3-binding peptide were linked, the impact of the type of the amino acid sequence of the CNGB3-binding peptide on the intensity of the cytotoxicity against endometriosis cells was examined.

Specifically, two types of peptides consisting of the amino acid sequences shown in Table 2 were synthesized, and cytotoxicity against A431-CNGB3-myc cells was compared. In the two types of peptides, the KLAK sequence and the HLAH sequence moiety were synthesized from D-amino acids, and the CNGB3-binding peptide moiety was synthesized with L-amino acids.

TABLE 1

|  | KLAK-HLAH | Seq. | Seq. No. |
|---|---|---|---|
| WT | 14 + 14 | KLAKLAK-KLAKLAK-HLAHLAH-HLAHLAH-VRRADNRPG | 8 |
| D5E | 14 + 14 | KLAKLAK-KLAKLAK-HLAHLAH-HLAHLAH-VRRAENRPG | 9 |

<Evaluation of Cytocidal Properties>

The cytocidal activity of each peptide was evaluated by measuring an ATP amount in A431-CNGB3-myc cells treated with each peptide using CellTiter-Glo (registered trademark) assay kit (manufactured by Promega).

Specifically, first, A431-CNGB3-myc cells after 2 passages were disseminated into a 96-well plate (manufactured by Corning/Costar, Lot No. 00515003) so as to be $1 \times 10^4$ cells/well by preparing the concentration of the cells. After culturing for 2 days after the dissemination, each peptide was added to each well such that a final concentration was 35.5, 75, or 150 μM, respectively, and cultured for 24 hours. Thereafter, the culture supernatant was removed from each well, and CellTiter-Glo buffer was added to the remaining cells, and after homogenization, the supernatant was recovered by centrifugation and used as a lysate. A double quantity of PBS and a 2×CellTiterGlo Reagent of the equivalent amount of the lysate were added to the lysate and stirred to obtain a reaction solution, and the reaction solution was stood at room temperature for 10 minutes. The luminescence intensity (Luminescence) (RLU: RELATIVE LIGHT UNITS) of the reaction solution after standing at room temperature was measured using a Synergy H1 hybrid multi-mode microplate reader (manufactured by BioTek Corporation). The luminescence intensity of the reaction solution is an indicator of the amount of ATP. It is shown that the smaller the luminescence intensity of the reaction solution is, the amount of ATP is small, and the cytocidal activity of the administered peptide is strong. All trials were measured in triplicate and the average was evaluated as the cytocidal activity at the concentration of each peptide.

In the evaluation of the cytocidal activity against the A431-CNGB3-myc cells of each peptide, the measurement result of the fluorescence intensity (RLU) of each reaction solution is shown in FIG. 1. In FIG. 1, the "WT" indicates the result of the peptide WT of Table 1, and the "D5E" indicates the result of the peptide D5E of Table 1, respectively. Both peptides commonly showed concentration-dependent cytocidal activity. The peptide WT in which the CNGB3-binding peptide is a Z13 peptide showed stronger cytocidal activity than the peptide D5E in which the CNGB3-binding peptide is a peptide of SEQ ID NO: 4.

Example 1

In the peptide in which the KLAK peptide, the HLAH peptide, and the Z13 peptide were linked, a length of the KLAK sequence and the HLAH sequence was optimized such that the intensity of cytotoxicity against the endometriosis cells became the maximum.

Specifically, 16 types of peptides consisting of an amino acid sequence shown in Table 2 was synthesized, and cytotoxicity against the A431-CNGB3-myc cells was compared. In the 16 types of peptides, the KLAK sequence and the HLAH sequence moiety were synthesized from D-amino acids, and the Z13 peptide moiety was synthesized with L-amino acids.

HLAH sequence. In addition, in the peptides 1 to 8, the shortest peptide 8 had stronger cytocidal activity than the longest peptide 1, and in the peptides 9 to 16, the shortest peptide 16 had stronger cytocidal activity than the longest peptide 9.

Example 2

The peptide 8 showing the strongest cytocidal activity in Example 1 was further shortened to optimize the intensity of the cytotoxicity against the endometriosis cells to the maximum.

Specifically, 14 types of peptides consisting of the amino acid sequences shown in Table 3 were synthesized, and cytotoxicity against A431-CNGB3-myc cells was compared. In the 14 types of peptides, the KLAK sequence and the HLAH sequence moiety were synthesized from D-amino acids, and the Z13 peptide moiety was synthesized with L-amino acids.

TABLE 2

| Peptide | | Seq. | Seq. No. |
|---|---|---|---|
| KLAK-HLAH | | | |
| 1 | 14 + 14 | KLAKLAK-KLAKLAK-HLAHLAH-HLAHLAH-VRRADNRPG | 8 |
| 2 | 14 + 13 | KLAKLAK-KLAKLAK-HLAHLAH-HLAHLA-VRRADNRPG | 10 |
| 3 | 14 + 12 | KLAKLAK-KLAKLAK-HLAHLAH-HLAHL-VRRADNRPG | 11 |
| 4 | 14 + 11 | KLAKLAK-KLAKLAK-HLAHLAH-HLAH-VRRADNRPG | 12 |
| 5 | 14 + 10 | KLAKLAK-KLAKLAK-HLAHLAH-HLA-VRRADNRPG | 13 |
| 6 | 14 + 9 | KLAKLAK-KLAKLAK-HLAHLAH-HL-VRRADNRPG | 14 |
| 7 | 14 + 8 | KLAKLAK-KLAKLAK-HLAHLAH-H-VRRADNRPG | 15 |
| 8 | 14 + 7 | KLAKLAK-KLAKLAK-HLAHLAH-VRRADNRPG | 16 |
| HLAH-KLAK | | | |
| 9 | 14 + 14 | HLAHLAH-HLAHLAH-KLAKLAK-KLAKLAK-VRRADNRPG | 17 |
| 10 | 14 + 13 | HLAHLAH-HLAHLAH-KLAKLAK-KLAKLA-VRRADNRPG | 18 |
| 11 | 14 + 12 | HLALLAH-HLAHLAH-KLAKLAK-KLAKL-VRRADNRPG | 19 |
| 12 | 14 + 11 | HLAHLAH-HLAHLAH-KLAKLAK-KLAK-VRRADNRPG | 20 |
| 13 | 14 + 10 | HLAHLAH-HLAHLAH KLAKLAK-KLA-VRRADNRPG | 21 |
| 14 | 14 + 9 | HLAHLAH-HLAHLAH-KLAKLAK-KL-VRRADNRPG | 22 |
| 15 | 14 + 8 | HLAHLAH-HLAHLAH-KLAKLAK-K-VRRADNRPG | 23 |
| 16 | 14 + 7 | HLAHLAH-HLAHLAH-KLAKLAK-VRRADNRPG | 24 |

Figure 2:
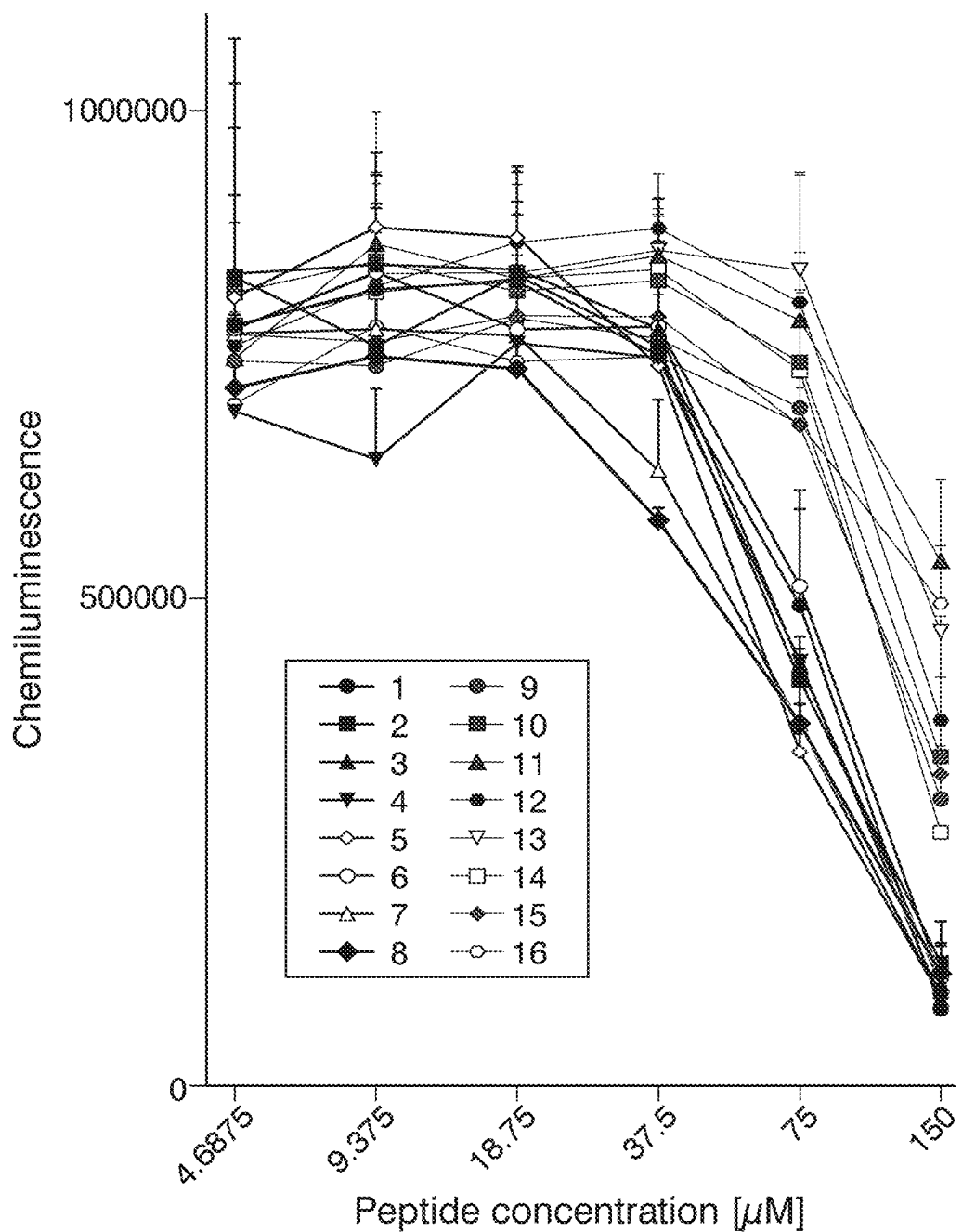
FIG. 2 is a view illustrating a measurement result of emission intensity (RIX) of a reaction solution treated with each peptide in Example 1.

The final concentration of each peptide added to the A431-CNGB3-myc cells disseminated into the 96-well plate was set to be 2.34, 4.69, 9.38, 18.8, 37.5, 75, or 150 µM, and the cytocidal activity of each peptide was evaluated in the same manner as that of Reference Example 1, except that the culture time after addition of the peptide was set to 20 hours. In the evaluation of the cytocidal activity against the A431-CNGB3-myc cells of each peptide, the measurement result of the fluorescence intensity (RLU) of each reaction solution is shown in FIG. 2. In the figure, "1" to "16" show the result of the reaction solution to which peptides 1 to 16 of Table 2 were added, respectively. All of them showed concentration-dependent cytocidal activity 20 hours after the addition of the peptide. The peptides 1 to 8 in which the peptide of the HLAH sequence is linked to a downstream of the peptide of the KLAK sequence showed stronger cytocidal activity than the peptides 9 to 16 in which the peptide of the KLAK sequence was linked to a downstream of the peptide of the

TABLE 3

| Peptide | KLAK-HLAH | Seq. | Seq. No. |
|---|---|---|---|
| 8 | 14 + 7 | KLAKLAK-KLAKLAK-HLAHLAH-VRRADNRPG | 16 |
| A1 | 14 + 6 | KLAKLAK-KLAKLAK-HLAHLA-VRRADNRPG | 25 |
| A2 | 14 + 5 | KLAKLAK-KLAKLAK-HLAHL-VRRADNRPG | 26 |
| A3 | 14 + 4 | KLNKLAK-KLAKLAK-HLAH-VRRADNRPG | |
| A4 | 14 + 3 | KLAKLAK-KLAKLAK-HLA-VRRADNRPG | |
| A5 | 14 + 2 | KLAKLAK-KLAKLAK-HL-VRRADNRPG | 29 |

TABLE 3 -continued

| Peptide | KLAK-HLAH | Seq. | Seq. No. |
|---|---|---|---|
| A6 | 14 + 1 | KLAKLAK-KLAKLAK-H-VRRADNRPG | 30 |
| B1 | 13 + 7 | KLAKLAK-KLAKLA-HLAHLAH-VRRADNRPG | 31 |
| B2 | 12 + 7 | KLAKLAK-KLAKL-HLAHLAH-VRRADNRPG | 32 |
| B3 | 11 + 7 | KLAKLAK-KLAK-HLAHLAH-VRRADNRPG | 33 |
| B4 | 10 + 7 | KLAKLAK-KLA-HLAHLAH-VRRADNRPG | 34 |
| B5 | 9 + 7 | KLAKLAK-KL-HLAHLAH-VRRADNRPG | 35 |
| B6 | 8 + 7 | KLAKLAK-K-HLAHLAH-VRRADNRPG | 36 |
| B7 | 7 + 7 | KLAKLAK-HLAHLAH-VRRADNRPG | 37 |

Figure 3:
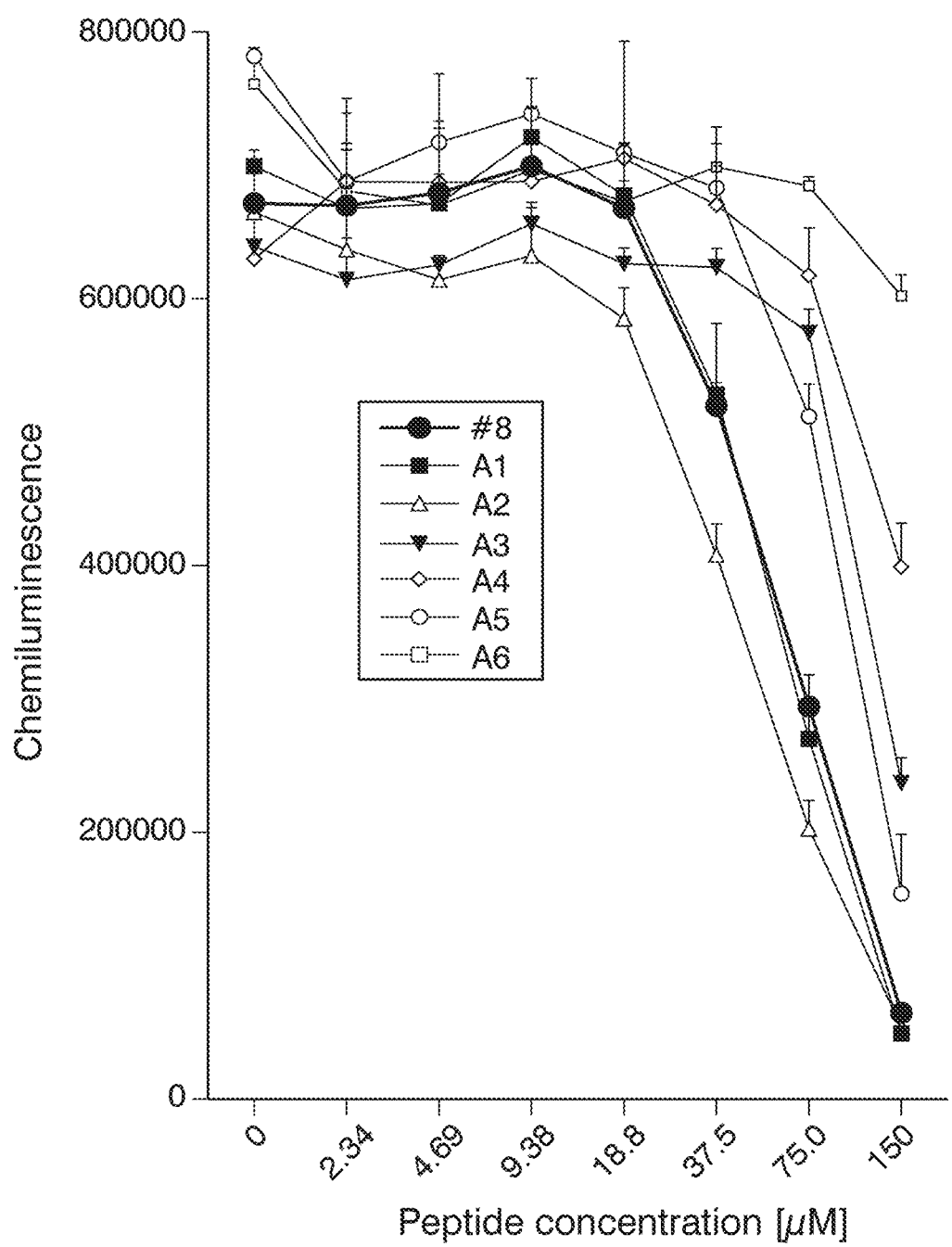
FIG. 3 is a view illustrating a measurement result of emission intensity (RLU) of a reaction solution treated with each peptide of a peptide 8 and peptides A1 to A6 in Example 2.
Figure 4:
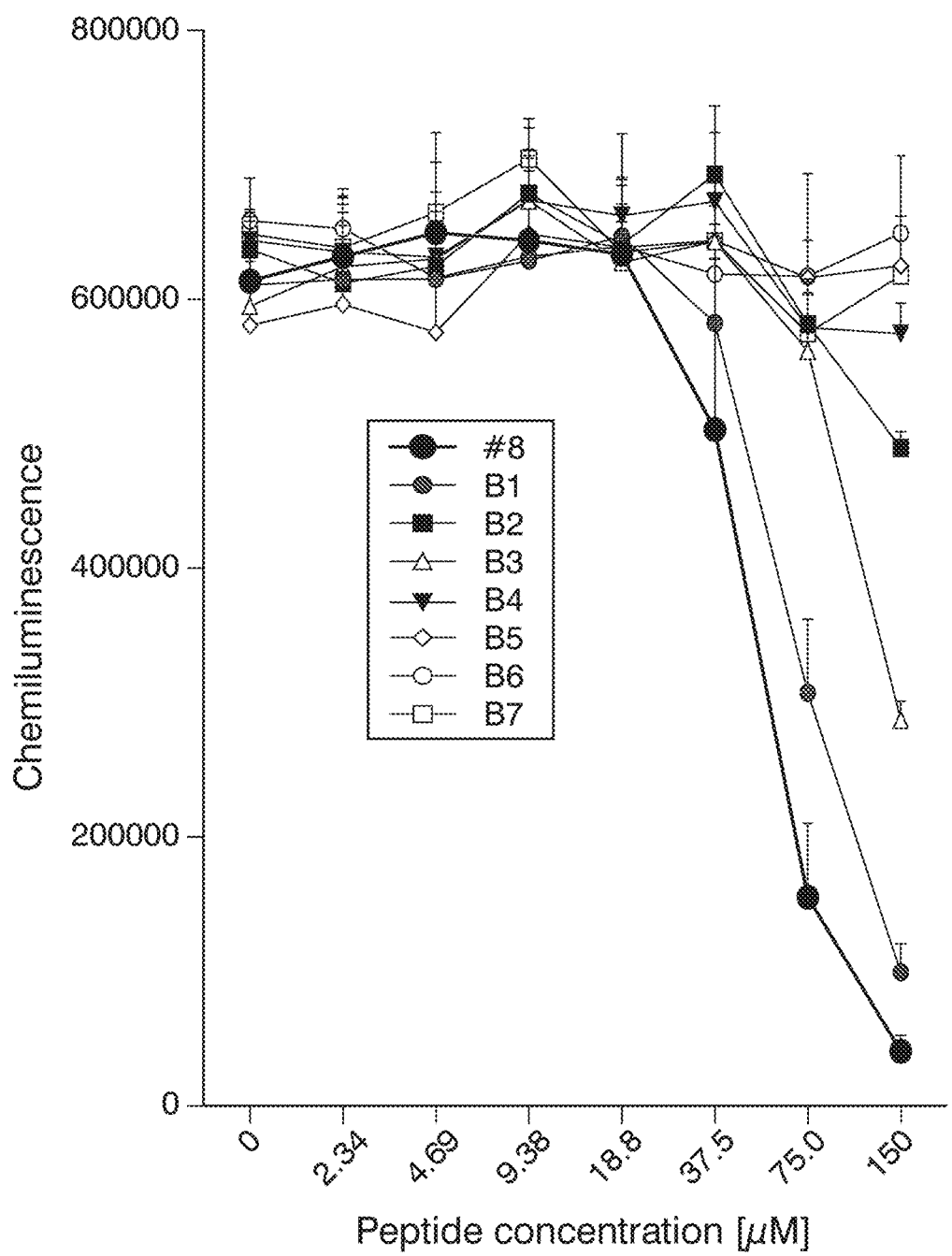
FIG. 4 is a view illustrating a measurement result of emission intensity (RLU) of a reaction solution treated with each peptide of the peptide 8 and peptides B1 to B7 in Example 2.

The cytocidal activity of each peptide was evaluated in the same manner as that of Example 1. In evaluation of the cytocidal activity against the A431-CNGB3-myc cells of each peptide, the measurement result of the fluorescence intensity (RLU) of the reaction solution treated with the peptide 8 and the peptides A1 to A6 was shown in FIG. 3, and the measurement result of the fluorescence intensity (RLU) of the reaction solution treated with the peptide 8 and the peptides B1 to B7 was shown in FIG. 4. In the figures, the "™8" represents the result of the reaction solution to which the peptide 8 of Table 3 was added, the "A1" to "A6" and "B1" to "B6" show the result of the reaction solution to which the peptides A1 to A6 and B1 to B6 of Table 3 were added, respectively. In the peptides A1 to A6 of which the KLAK sequence consisted of 14 amino acids, the peptides A3 to A6 of Which the HLAH sequence consisted of 4 amino acids or less showed cytocidal activity even when the peptide final concentration was 75 UM (FIG. 3). In addition, in the peptides B1 to B7 of which the HLAH sequence consisted of 7 amino acids, the peptides B3 to B7 of which the KLAK sequence consisted of 11 amino acids or less showed cytocidal activity even when the peptide final concentration was 75 µM (FIG. 4). In addition, only the peptide A2 showed stronger cytocidal activity than the peptide 8. From the results, it was recognized that as the effector peptide, a peptide in which a peptide of which the KLAK sequence consists of 14 amino acids and a peptide of which the HLAH sequence consists of 5 amino acids were linked showed the highest cytocidal activity.

Example 3

In the peptide in which the KLAK peptide, the HLAH peptide, and the Z13 peptide were linked, the intensity of the cytocidal activity in a case where the constituent amino acid was D-amino acid and in a case where the constituent amino acid was L-amino acid was examined.

Specifically, intensity of the cytocidal activity of the peptide A2 (both of the KLAK sequence consisting of 14 amino acids and the HLAH sequence consisting of 5 amino acids include D-amino acids. It is referred to as a peptide (14D+5D)) described in Table 3, a peptide (14D+5L) in which in the amino acids of the peptide 8, the KLAK sequence consisting of 14 amino acids includes D-amino acids, and the HLAH sequence consisting of 5 amino acids include L-amino acids, a peptide (14L+5D) in which in the amino acids of the peptide 8, the KLAK sequence consisting of 14 amino acids include L-amino acids, and the HLAH sequence consisting of 5 amino acids include D-amino acids, and a peptide (14L+5L) in which all of the amino acids of the peptide 8 include L-amino acids was examined in the same manner as that of Example 1. All of the Z13 peptide moiety of these peptides include only L-amino acids.

Figure 5:
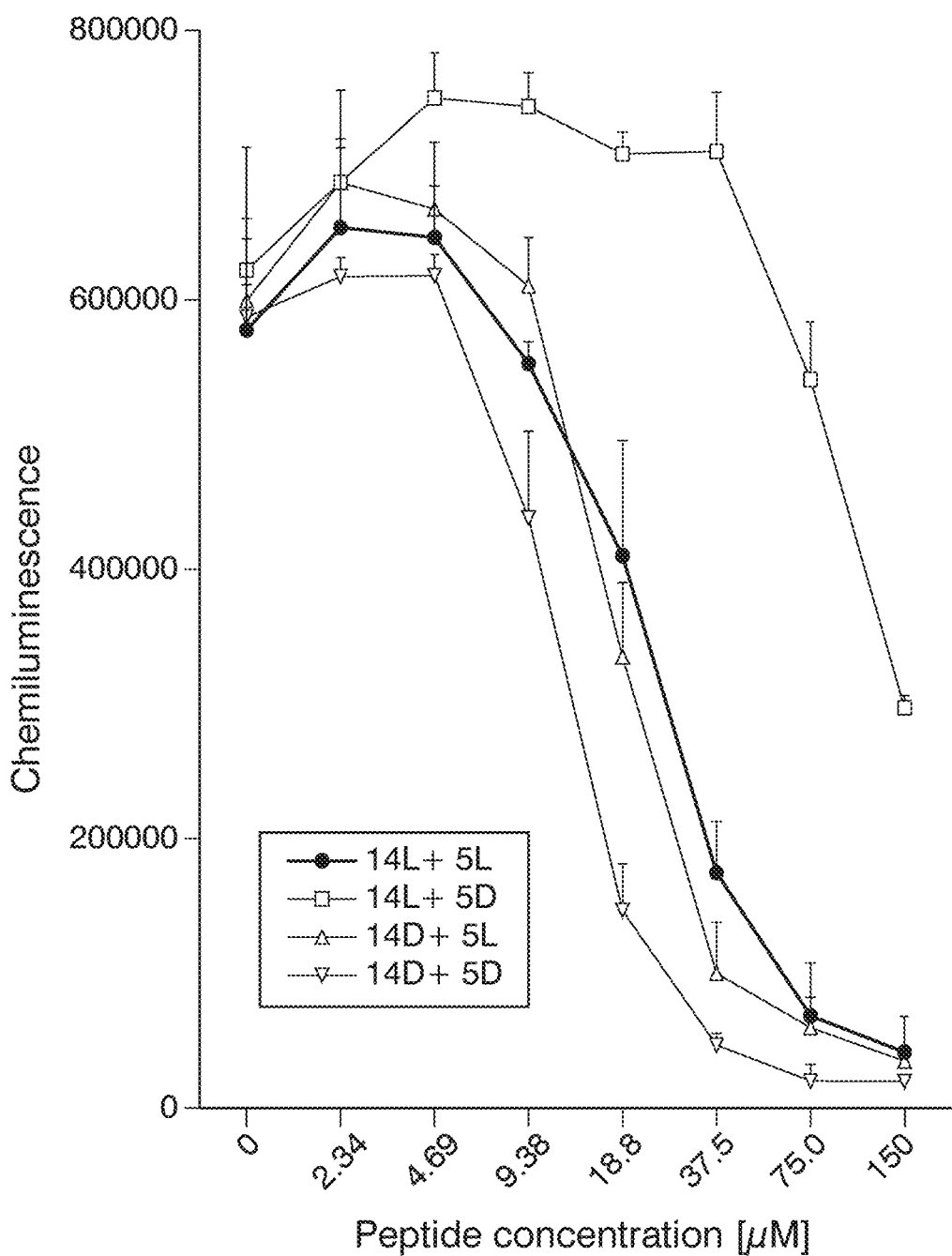
FIG. 5 is a view illustrating a measurement result of emission intensity (RLU) of a reaction solution treated with each peptide in Example 3.

In the evaluation of the cytocidal activity against the A431-CNGB3-myc cells of each peptide, the measurement result of the fluorescence intensity (RLU) of the reaction solution treated with each peptide was shown in FIG. 5. The cytocidal activity of the peptide (14L+5L) in which all of the escape peptides include L-amino acids was the lowest, and the cytocidal activity of the peptide A2 (peptide (14D+5D)) in which all of the escape peptides include D-amino acids was the highest. It was estimated that the peptide consisting of D-amino acids was hardly digested in the endosome or the cytoplasm than the peptide consisting of L-amino acids, and the endosome escape activity and the apoptosis-inducing activity were sufficiently exhibited.

Example 4

The cytocidal activity of the peptide A2 in which the cytocidal activity was the highest was examined in Examples 2 and 3.

<Quantitative Analysis of Alive Cells>

Figure 6:
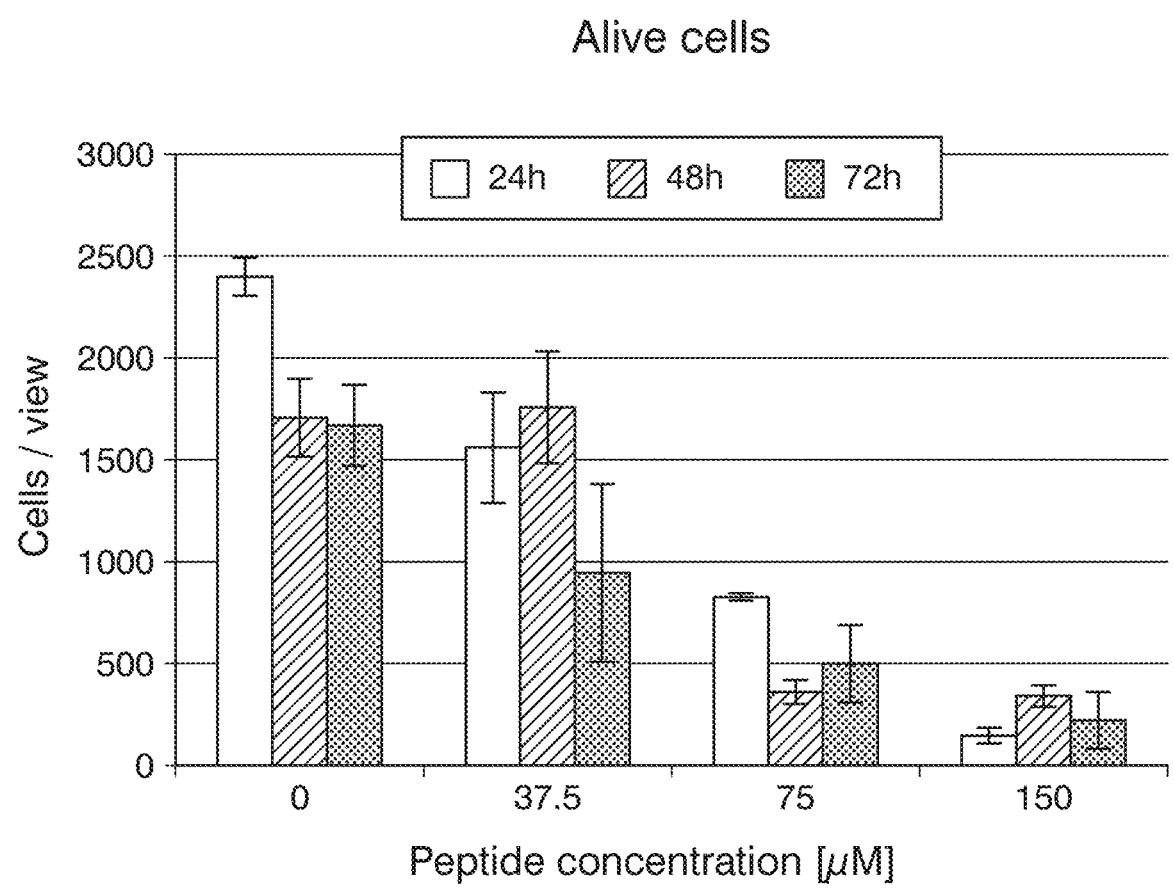
FIG. 6 is a view illustrating a measurement result of the number of alive cells of A431-CNGB3-myc cells treated with a peptide A2 in Example 4.

The A431-CNGB3-myc cells disseminated on a cover glass placed in a multi-dish for cell culture were added such that the final concentration of the peptide A2 was 0 (control), 37.5, 75, or 150 and cultured. After 24, 48, or 72 hours from the addition of the peptide, the number of cells (alive cells) adhered and spread onto the cover glass were counted. The measurement result of the number of the alive cells (Cells/view) per single visual field is shown in FIG. 6. As a result, it was determined that the number of the alive cells of the A431-CNGB3-myc cells was decreased dependent on the concentration of the added peptide A2 over time.

<Analysis of Apoptosis-Inducing Activity>

Figure 7:
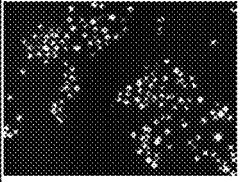
FIG. 7 is a staining image in which Apop-Tag assay and nuclear staining were performed on the A431-CNGB3-myc cells treated with the peptide A2 in Example 4.

The A431-CNGB3-myc cells disseminated on a cover glass placed in a multi-dish for cell culture were added such that the final concentration of the peptide A2 was 0 (control), 37.5, 75, or 150 µM, and cultured. After 24, 48, or 72 hours from the addition of the peptide, apoptosis was detected by using ApopTag (registered trademark) Fluorescein In Situ Apoptosis Detection Kit. FIG. 7 shows the result in which Apop-Tag assay was performed on the cells after 48 hours from the addition of the peptide. In the figure, the "Hoechst" represents the result of nuclear staining with a Hoechst 33342 solution. As a result, dependent on the concentration of the added peptide A2, it was confirmed that the number of the Apop-Tag stained cells was large, and apoptosis was induced by the peptide A2.

Example 5

The peptide A2 which has the highest cytocidal activity in Examples 2 and 3 was administered to the endometriosis model mouse, and a therapeutic effect on endometriosis was examined.

<Single Administration of Peptide into Peritoneal Cavity>

0.5 mL of a physiological saline solution heated to 37° C. in the peritoneum was put into the endometriosis model mouse after 7 days from transplanting the A431-CNGB3-myc cells into the peritoneal cavity under isoflurane anesthesia, and immediately after massaging, the peptide 42 was dissolved in the physiological saline solution and the solution was administered into the peritoneum. The peptide A2 was administered such that an administration amount per mouse weight was 0 mg/10 mL/kg (control), 5 mg/10 mL/kg, or 10 mg/10 mL/kg (n=3).

<Multiple Administration of Peptide to Peritoneal Cavity>

0.5 mL of a physiological saline solution heated to 37° C. in the peritoneum was put into the endometriosis model mouse after 7 days from transplanting the A431-CNGB3-myc cells into the peritoneal cavity under isoflurane anesthesia, and immediately after massaging, the peptide A2 was dissolved in the physiological saline solution and the solution was administered into the peritoneum (single administration). Thereafter, after 8 and 9 days from transplanting the A431-CNGB3-myc cells into the peritoneal cavity, the peptide A2 solution was administered in the same manner. That is, the peptide A2 solution was administered once a day, a total of three times. The peptide A2 was administered such that an administration amount per mouse weight was 0 mg/1.0 mL/kg (control), 2.5 mg/1.0 mL/kg, 5.0 mg/10 mL/kg, or 7.5 mg/10 mL/kg n=3).

<Collection of Peritonea (Material Collection)>

The endometriosis model mouse into which the peptide A2 was administered died of bleeding under isoflurane anesthesia after 24 hours or 48 hours from the final administration to collect the peritoneum. The peritoneum for ATP measurement was frozen with liquid nitrogen, and stored in a deep freezer until the measurement. A peritoneum for pathological specimen preparation was immersed and fixed in 10% neutral buffer formalin, respectively, and refrigerated.

A weight of each mouse was measured before being died of bleeding. There was no particular change in the weight of each mouse regardless of the administration amount or the number of administrations of the peptide A2.

<Measurement of ATP Amount>

The measurement of the ATP amount was performed by using a CellTiter-Glo (registered trademark) assay kit (manufactured by Promega). The weight of the frozen peritoneum was measured, and 10 times the quantity of CellTiter-Glo buffer of the frozen tissue was added, and after homogenization, the supernatant was recovered by centrifugation and used as a lysate. A double quantity of PBS and a 2×CellTiterGlo Reagent of the equivalent amount of the lysate were added to the lysate and stirred to obtain a reaction solution, and the reaction solution was stood at room temperature for 10 minutes. The luminescence intensity (RLU) of the reaction solution after standing at room temperature was measured using a Synergy H1 hybrid multi-mode microplate reader (manufactured by BioTek Corporation). It is shown that the luminescence intensity of the reaction solution is an indicator of the amount of ATP, and the smaller the luminescence intensity of the reaction solution is, the amount of ATP is small, and the cytocidal activity of the administered peptide is strong. All trials were measured in triplicate (n=3) and the average was evaluated as the cytocidal activity of each peptide.

Figure 8:
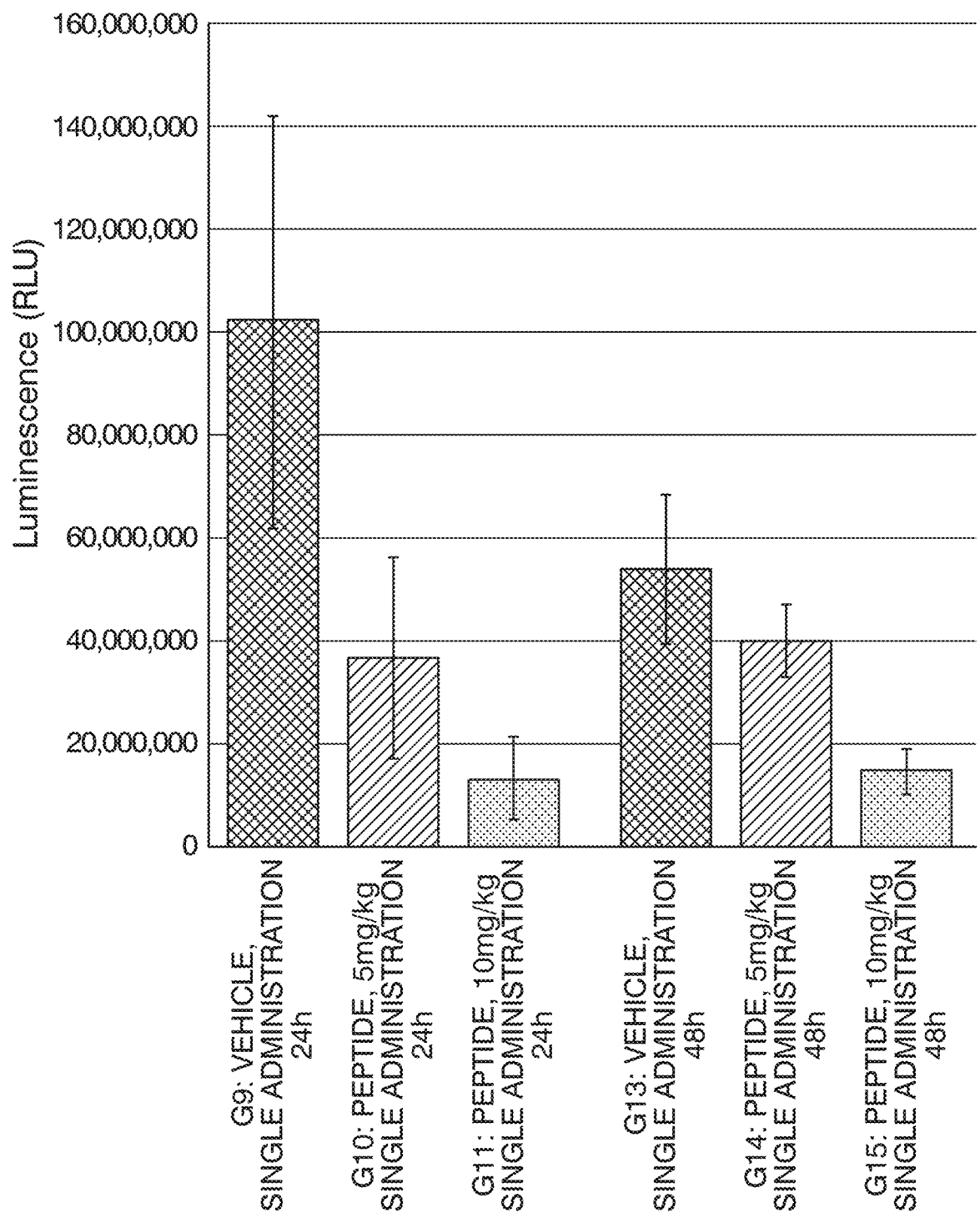
FIG. 8 is a view illustrating a measurement result of emission intensity (RLU) of peritoneum of an endometriosis model mouse in which the peptide A2 was administered in the peritoneal cavity one time in Example 5.
Figure 9:
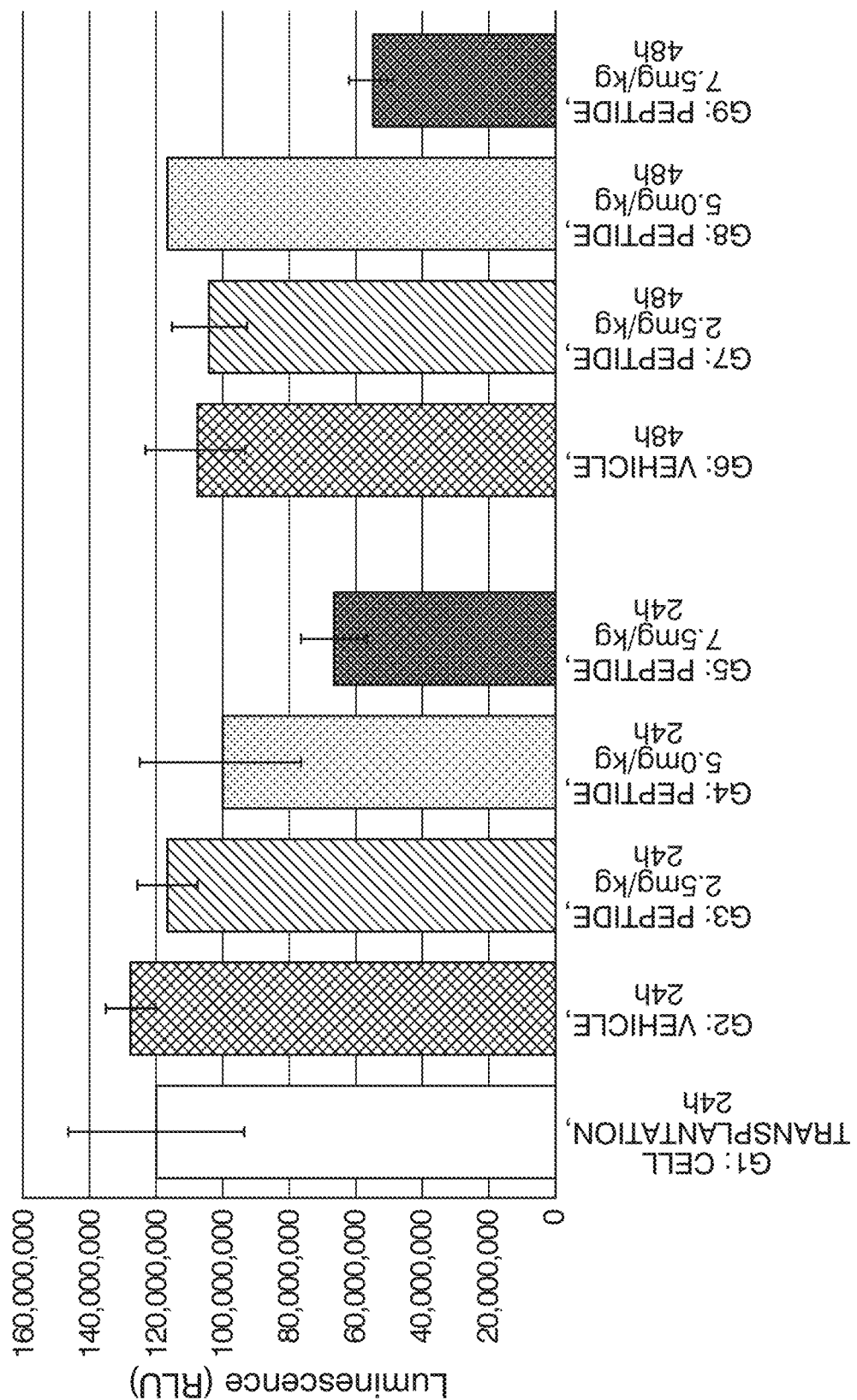
FIG. 9 is a view illustrating a measurement result of emission intensity (RLU) of peritoneum of an endometriosis model mouse in which the peptide A2 was administered in the peritoneal cavity multiple times in Example 5.
Figure 10:
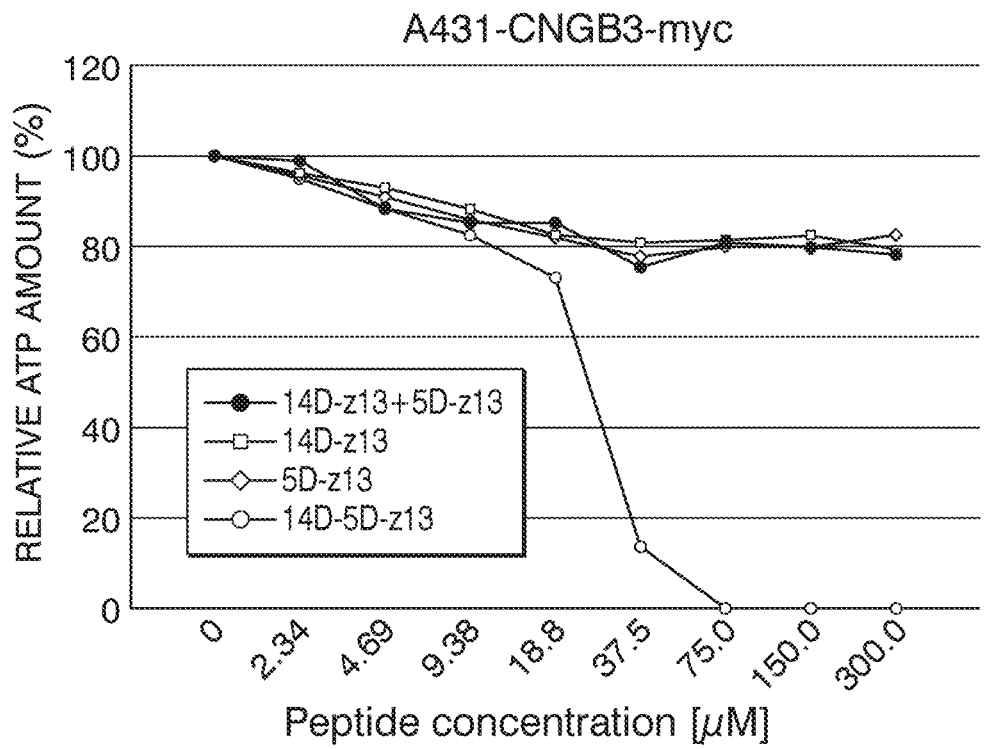
FIG. 10 is a view illustrating a measurement result of a relative ATP amount (%) of the A431-CNGB3-myc cells treated with each peptide in Example 6.
Figure 11:
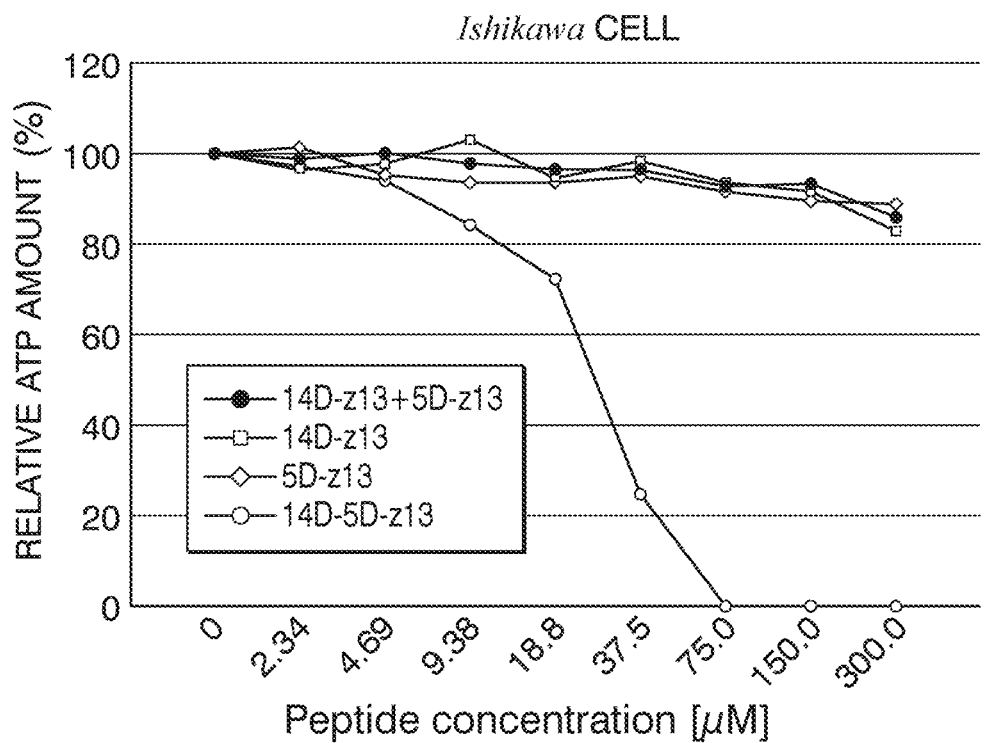
FIG. 11 is a view illustrating a measurement result of a relative ATP amount (%) of Ishikawa cells treated with each peptide in Example 6.
Figure 12:
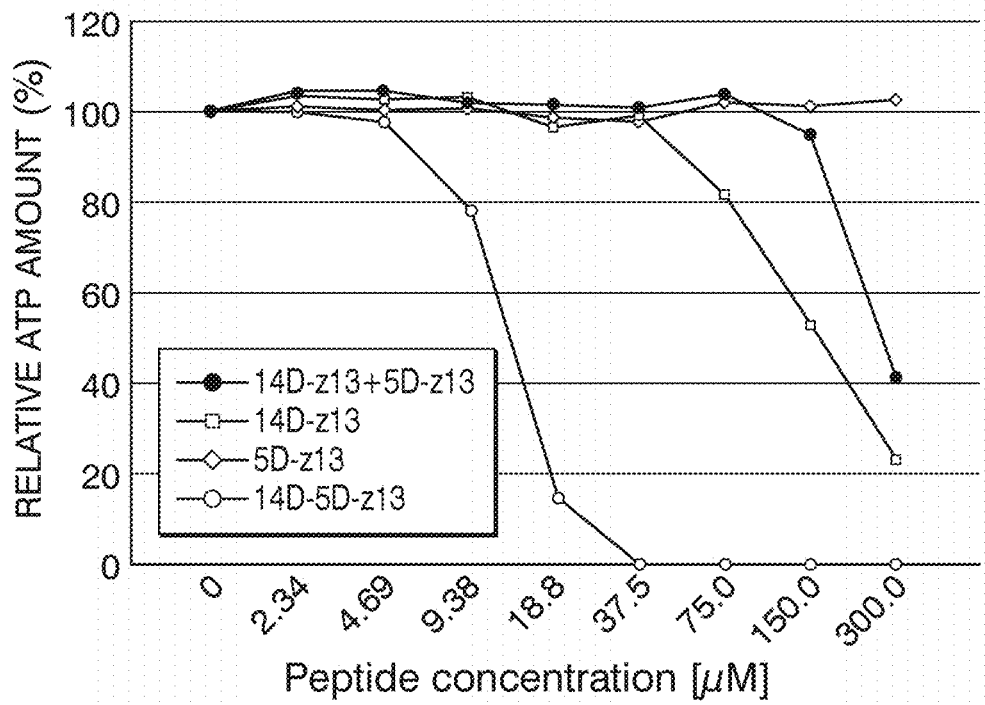
FIG. 12 is a view illustrating a measurement result of a relative ATP amount (%) of SNG-H cells treated with each peptide in Example 6.
Figure 13:
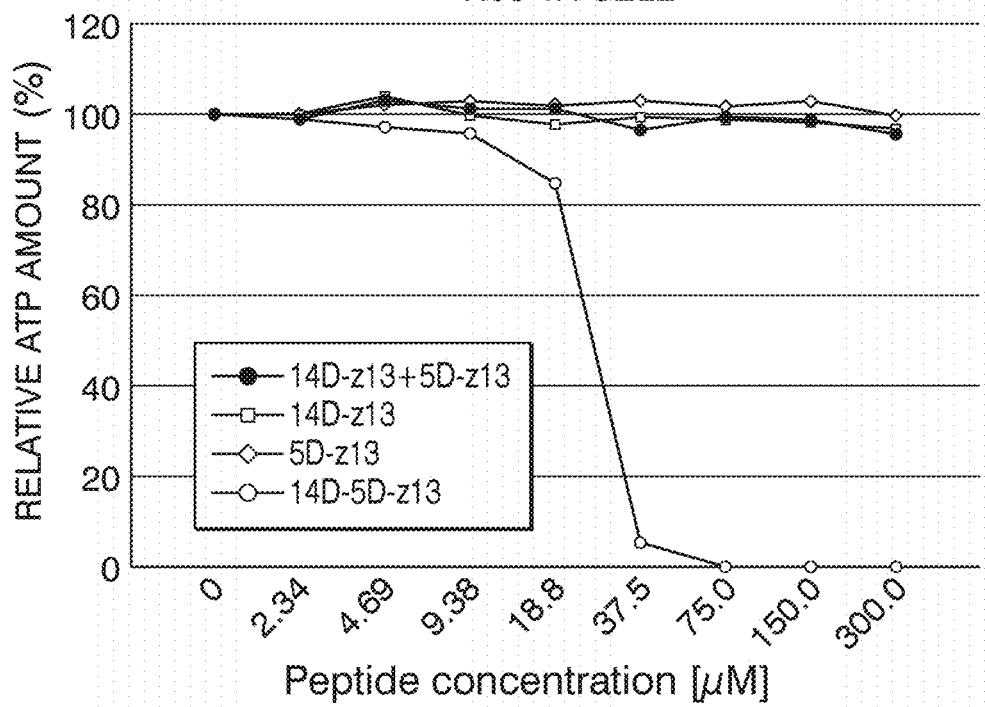
FIG. 13 is a view illustrating a measurement result of a relative ATP amount (%) of Hec-1A cells treated with each peptide in Example 6.
Figure 14:
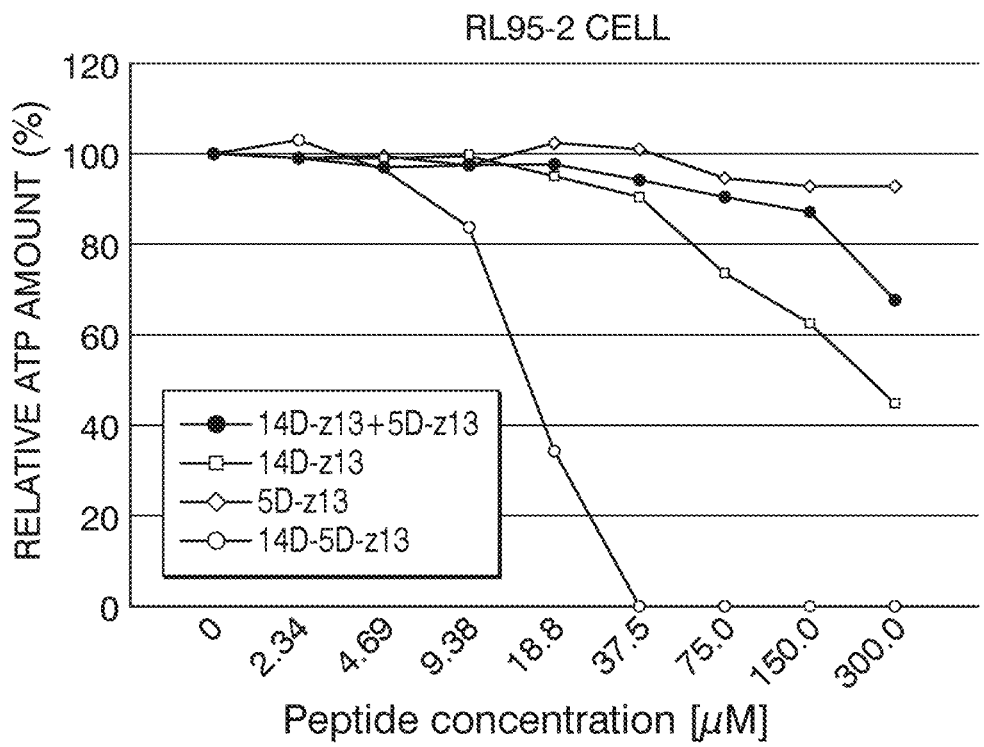
FIG. 14 is a view illustrating a measurement result of a relative ATP amount (%) of RL95-2 cells treated with each peptide in Example 6.

The measurement result of the luminescence intensity (RLU) of the peritoneum of the endometriosis model mouse into which the peptide A2 was administered once is shown in FIG. 8. In addition, the measurement result of the luminescence intensity (RU) of the peritoneum of the endometriosis model mouse into which the peptide A2 was repeatedly administered three times is shown in FIG. 9. As shown in FIGS. 8 and 9, in any of a mouse to which administration was performed once and a mouse to which administration was performed multiple times, it was confirmed that the luminescence intensity (RLU) of the peritoneum was decreased dependent on the administered peptide A2 amount, and the amount of MP in the peritoneum was decreased. The decrease in the amount of ATP in the peritoneum means reduction of the number of the alive cells of the A431-CNGB3-myc cells transplanted into the peritoneum. From the result, it can be said that the A431-CNGB3-myc cells in the peritoneal cavity was killed by the peptide A2, that is, the peptide A2 can exhibit cytocidal effect in an in-vivo environment, and is particularly useful as a therapeutic agent for endometriosis.

<TUNEL Staining>

HE staining and TUNEL staining were performed on the peritoneum for pathological specimen preparation fixed with 10% neutral buffer formalin. As a result, it was confirmed that a peptide A2 administration group is TUNEL method (TdT-mediated Dutp nick end labeling) positive (not illustrated), and the peptide A2 induces apoptosis and shows a cytocidal effect.

Example 6

A cytocidal activity of the peptide A2 (peptide (14D+5D)) to the A431-CNGB3-myc cells and a cell strain derived from various uterine cancer cells was examined.

As the cancer-derived cell strain, an Ishikawa cell derived from human endometrium gland cancer, an SNG-II cell derived from human endometrium cancer, an Hec-1A cell derived from human uterine body cancer, and a RL95-2 cell derived from human endometrium cancer were used. The cells were cultured in the same manner as the A431-CNG133-myc cells.

As the peptide treating each cell, three types of peptides consisting of amino acid sequences shown in Table 4 were used. In the three types of peptides, the KLAK sequence and the HLAH sequence moiety were synthesized from D-amino acids, and the Z13 peptide moiety was synthesized with L-amino acids.

TABLE 4

|      | KLAK-HLAH-Z13 | Seq.          | | Seq. No. |
|------|---------------|---------------|---|----------|
| A2   | 14D + 5D + Z13 | KLAKLAK-KLAKLAK-HLAHL-VRRADNRPG | | 26 |
| A2-1 | 14D + Z13     | KLAKLAK-KLAKLAK-VRRADNRPG | | 38 |
| A2-2 | 5D + Z13      | HLAHL-VRRADNRPG | | 39 |

The cytocidal activity of each peptide was evaluated in the same manner as that of Example 1, except that the final concentration of each peptide added to each cell disseminated into the 96-well plate was set to be 0 (peptide non-added), 2.34, 4.69, 9.38, 18.8, 37.5, 75.0, 150.0, or 300.0 μM. A relative fluorescence intensity (%) of each reaction solution in a case Where the fluorescence intensity (RLU) of the reaction solution to which no peptide was added was set to 100% was calculated as a relative ATP amount (%). The calculation result is shown in FIGS. 10 to 14. In the figure, the "14D–Z13+5D–Z13" represents a relative ATP amount of the reaction solution to which both of a peptide A2-1 and a peptide A2-2 were added, the "14D–Z13" represents a relative ATP amount of the reaction solution to which only the peptide A2-1 was added, the "5D–Z13" represents a relative ATP amount of the reaction solution to Which only the peptide A2-2 was added, and the "14D–5D–Z13" represents a relative ATP amount (%) of the reaction solution to which only the peptide A2 was added, respectively. As shown in FIGS. 10 to 14, it was confirmed that the peptide A2 has cytocidal activity to not only the A431-CNGB3-myc cells but also various cell strains derived from a uterine cancer cell. In addition, in the cell treated with both of a peptide in which the KLAK peptide and the Z13 peptide were linked and a peptide in Which the HLAH peptide and the Z13 peptide were linked, similar to the cell treated only with the peptide in which the KLAK peptide and the Z13 peptide were linked and the cell treated only with the peptide in which the HLAH peptide and the Z13 peptide were linked, the cytocidal activity was hardly observed or significantly weak.

Example 7

Since the A431 cells are epithelial-like cell cancer-derived cell strains, the endometriosis model mouse in which the A431-CNGB3-myc cells were transplanted into the peritoneal cavity is a cancer-bearing mouse. Here, a peptide (IFLLWQR-RR-KLAKLAK-KLAKLAK-HLAHL, SEQ II) NO: 40) in which an effector peptide consisting of an amino acid sequence represented by SEQ ID NO: 1 and an IF7 peptide are linked (hereinafter, referred to as "IF7 (RR)–(K+H) peptide") was administered to the peritoneal cavity of the endometriosis model mouse, and the cytocidal activity to cancer cells was examined. In the IF7 (RR)–(K+H) peptide, the KLAK sequence and the HLAH sequence moiety were synthesized with D-amino acids, and other peptide moieties were synthesized with L-amino acids.

<Tail Vein Administration of Peptide>

50 μL of a solution obtained by dissolving the IF7 (RR)–(K+H) peptide in a physiological saline solution was administered into an endometriosis model mouse after 14 days from transplanting the A431-CNGB3-myc cells into the peritoneal cavity once a day for six consecutive days via a tail vein. The IF7 (RR)–(K+H) peptide was administered such that an administration amount per mouse weight was 0 μg/body (control), 10 μg/body, or 50 μg/body.

As a result, in the control group into which a peptide was not administered (n=8), the number of dead individuals after 24 days from transplanting the A431-CNGB3-myc cells into the peritoneal cavity was 1, and the alive rate was 88.9%. With respect to this, in a group into which the IF7 (RR)–(K+H) peptide was administered such that the IF7 (RR)–(K+H) peptide was 10 μg/body/day or 50 μg/body (n=6), the alive rate was 100%. In addition, at the time of the end of the test, the spread of cancer cells (A431-CNGB3-myc cells) in the peritoneal cavity of all mice was examined. In contrast, in the control group, the cancer cells relatively spread throughout the whole peritoneum, and in the group into which the IF7 (RR)–(K+H) peptide was administered, the spread of cancer cells in many mice was relatively limited. There was no particular change in the weight of each mouse regardless of the administration amount or the number of administrations of the IF7 (RR)–(K+H) peptide. From the result, it was recognized that the intravenously administered IF7 (RR)–(K+H) peptide has cytocidal activity to cancer cells and is useful as an anti-cancer drug.

Example 8

The IF7 (RR)–(K+H) peptide used in Example 7 was intravenously administered to a cancer-bearing mouse in which a tumor was formed in the back, and cytocidal activity to cancer cells was examined.

<Luciferase Gene-Transferred Ovarian Cancer Cancer-Bearing Subcutaneous Tumor Mouse (OVCAR3-Luc Mouse)>

As the tumor tissue to be transplanted into a mouse, a tumor tissue obtained by culturing a luciferase gene-introduced ovarian cancer cell strain (OVCAR3-Luc cells, transferred from another facility) was used. Culturing of OVCAR3-Luc cells was performed at 37° C. in a 5 volume % carbon dioxide environment using RPMI medium 1640 (11875-093, gibe by life technologies) as a culture medium.

Approximately $1 \times 10^6$ OVCAR3-Luc cells were transplanted into the back of an eight-week female SCID mouse (C.B-17/Icr-scid/scid Jcl family, supplied by CLEA Japan, Inc.) to prepare an OVCAR3-Luc mouse.

<Tail Vein Administration of Peptide>

In the same manner as that of Example 7, 50 μL of a solution obtained by dissolving the IF7 (RR)–(K+H) peptide in a physiological saline solution was administered into the OVCAR3-Luc mouse once a day for six consecutive days via a tail vein. The IF7 (RR)–(K+H) peptide was administered such that an administration amount per mouse weight was 0 μg/body (control) or 10 μg/body.

<Measurement of Size of Tumor Tissue>

Each mouse was subjected to a luminescence imaging test, and the number of photons of the tumors on the back and the size of the tumor tissue were measured over time.

(1) Measurement of the Number of Photons

Measurement was performed using an in vivo luminescence imaging apparatus (Xenogen IVIS-200, manufactured by Caliper Corporation) using a luciferin-luciferase luminescence mechanism. First, 100 μL of a 30 mg/mL potassium D-luciferin (126-05116, manufactured by Wako Pure Chemical Industries, Ltd.) solution was administered to the peritoneal cavity of the OVCAR 3-Luc mouse. After 15 minutes from the administration, the mouse was measured with the in vivo luminescence imaging apparatus, and the number of photons was counted.

(2) Measurement of Tumor Volume

The estimated tumor volume (mm³) on the back of each OVCAR3-Luc mouse was obtained from the long diameter of the tumor by the following equation. The long diameter (mm) and the short diameter (mm) of the tumor were measured using a caliper.

[Estimated tumor volume (mm3)]=[long diameter (mm)]×[short diameter (mm)]×[short diameter (mm)]×½

Figure 15:
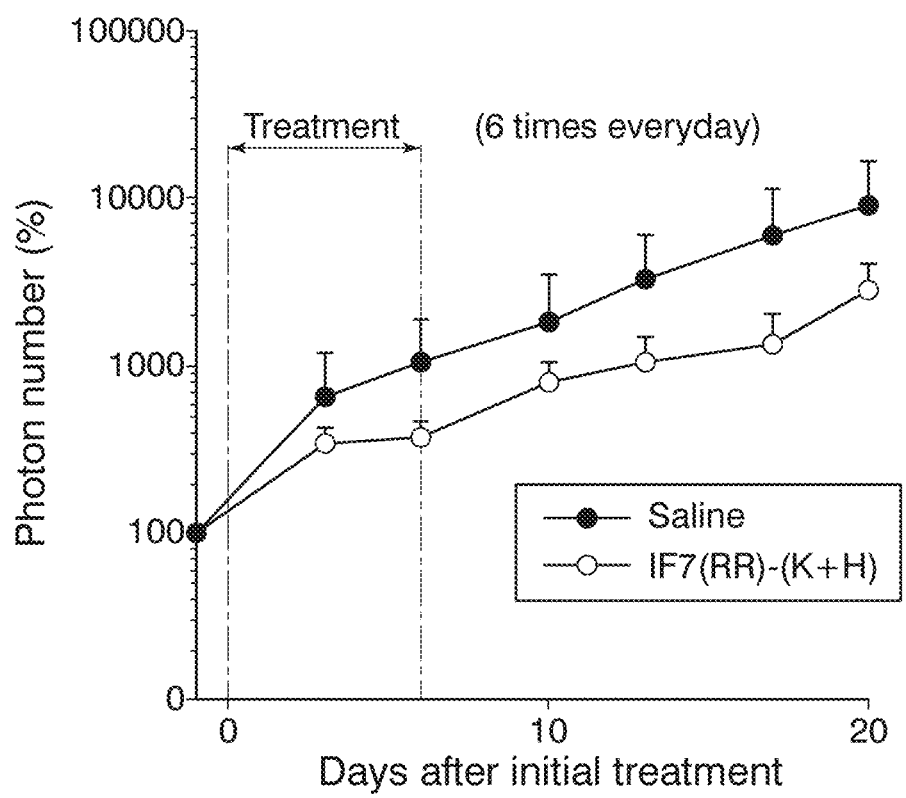
FIG. 15 is a view illustrating a result of time-dependently measuring an increase rate (%) of the number of photons of a cancer-carrying mouse to which an IF7 (RR)–(K+H) peptide is administered in Example 8.
Figure 16:
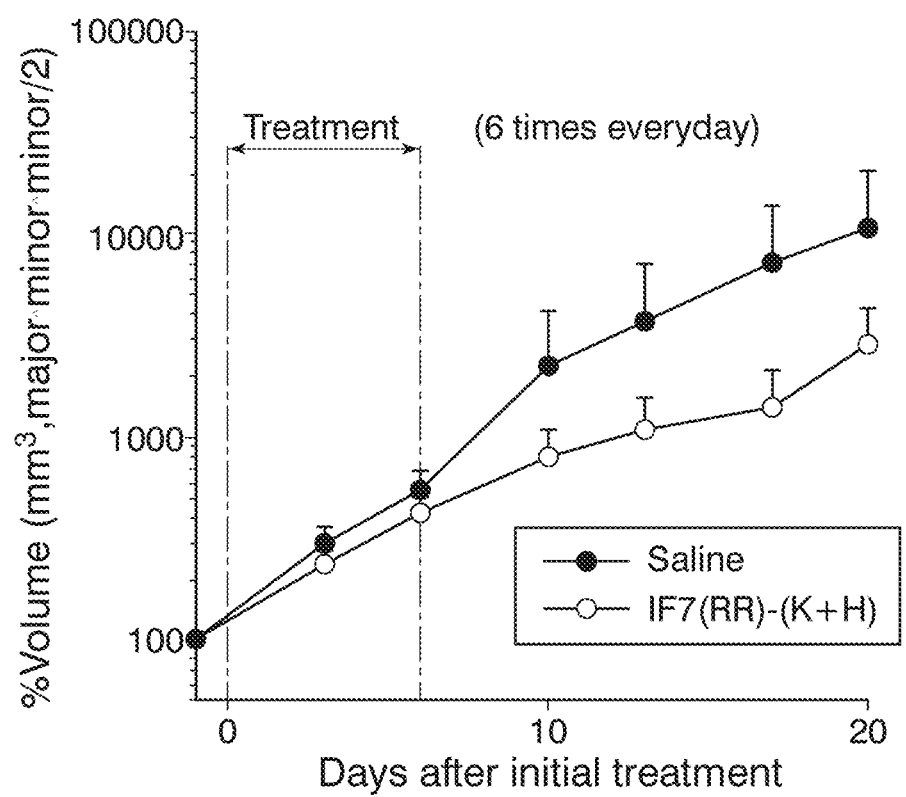
FIG. 16 is a view illustrating a result of time-dependently measuring an increase rate (%) of a tumor volume of the cancer-carrying mouse to which the IF7 (RR)–(K+H) peptide is administered in Example 8.

FIG. 15 shows a temporal change in an increase rate (%) in the number of the photons of the tumor on the back of each mouse, and FIG. 16 shows a temporal change in an increase rate (%) of the tumor volume (mm³) on the back of each mouse. Both of the increase rate of the number of the photons and the increase rate of the tumor volume were based on the value of the peptide solution on the day before the administration starting date (100%). In the figure, the "treatment" represents a treatment period in which the peptide solution was intravenously administered. As shown in FIG. 15, in the mouse treated with the IF7 (RR)–(K+H) peptide, the number of the photons was hardly increased during the peptide treatment period, and the increase rate after the peptide treatment period was also smaller than the control group (Saline). In addition, although there was no difference in the tumor volume between the control group and the IF7 (RR)–(K+H) peptide administration group during the peptide treatment period, the increase rate after the treatment period of the IF7 (RR)–(K+H) peptide administration group was apparently smaller. From the result, it can be said that administration of the IF7 (RR)–(K+H) peptide can kill the tumor tissue in vivo, and the peptide is useful as an anti-cancer drug.

Reference Example 2

Paraffin-embedded sections of cancer tissues of various organs were immunostained with an anti-CNGB3 antibody to examine presence or absence of the expression of CNGB3. As the tissue sections, two types (OV20811 and OV2088) among four types of commercially available human ovarian cancer tissue array (Ovary cancer tissue array (manufactured by US Biomax) and two types (FDA800a and MC964a) among cancer tissue arrays (Multiple organ tumor tissue array) of various organs were used. In addition, as the anti-CNGB3 antibody, among commercially available antibodies, two types of Biorbyt (Catalog No. orb 156415 BRT 100UG) (hereinafter, referred to as "antibody orb" sometimes) and Osenses (Code; OSC00253W) (hereinafter, referred to as "antibody 253W" were used).

Immunostaining of tissue sections was performed as follows. First, a paraffin-embedded tissue section was reacted with a blocking agent for liquid immunity test (Ommunoblock, manufactured by DS Pharma Biomedical Co., Ltd.) for 30 minutes to block non-specific reaction, and then washing treatment was performed twice with TBST (Tris buffer physiological saline containing Tween 20) for 5 minutes. Then, the tissue section was immersed in 0.3% hydrogen peroxide water, reacted for 5 minutes, blocked for endogenous peroxidase activity, and washed twice for 5 minutes with TBST. Subsequently, the tissue section was immersed in a 0.3% hydrogen peroxide solution, reacted for 5 minutes, and then subjected to blocking treatment of internal peroxidase activity. Thereafter, washing treatment was performed with TBST twice for 5 minutes. Subsequently, the tissue section was immersed in a primary antibody solution obtained by diluting the anti-CNGB3 antibody 100 times with REAL Antibody Diluent (Code 52022, manufactured by Dako Corporation) and reacted at room temperature for 30 minutes, and then washing treatment was performed twice with TBST for 5 minutes. In addition, the tissue section was reacted with a labeled secondary antibody (EnVision+System-HRP-labeled Polymer anti-rabbit antibody, manufactured by Dako Corporation) for 30 minutes at room temperature, and then washing treatment was performed twice with TBST for 5 minutes. Thereafter, the tissue section was treated with a DAB coloring reagent [DAB+Liquid (large size), RUO (K3468), manufactured by Dako Corporation] for 5 minutes to develop color. The tissue section after DAB coloring was washed with water, treated with Mayer's hematoxylin for 2 minutes to stain nuclei, and then sealed.

The staining result of OV20811 among human ovarian cancer tissue arrays is shown in Tables 5 to 10, and the staining result of OV2088 is shown in Tables 11 to 16, respectively. The staining result of FDA800a among cancer tissue arrays of various organs is shown in Tables 17 and 18, and the staining result of MC964a is shown in Tables 19 to 21, respectively. In the tables, in the column of each anti-CNGB3 antibody, "+" means the result of immunostaining with the antibody, and "−" means the result of no immunostaining with the antibody, respectively. It was recognized that most tissue sections were immunostained with the anti-CNGB3 antibody and CNGB3 was expressed.

TABLE 5

| | OV20811 | Grade | Stage | orb | 253W |
|---|---|---|---|---|---|
| 1 | Serous adenocarcinoma | 1 | Ia | + | + |
| 2 | Serous adenocarcinoma | | I | − | − |
| 3 | Adenocarcinoma (sparse) | — | Ia | + | + |
| 4 | Serous papillary adenocarcinoma | 2 | II | + | + |
| 5 | Serous papillary adenocarcinoma | | Ia | − | + |
| 6 | Mucinous papillary adenocarcinoma | 1 | Ic | − | + |
| 7 | Mucinous papillary adenocarcinoma (fibrous tissue and blood vessel) | — | Ia | + | + |
| 8 | Mucinous papillary adenocarcinoma | 1 | | + | − |
| 9 | | | | − | − |
| 10 | | | | + | + |
| 11 | | | IIa | + | + |
| 12 | Serous papillary adenocarcinoma | 2 | Ic | + | + |
| 13 | | | Ib | + | − |
| 14 | | | IIIc | + | + |
| 15 | | | | + | + |
| 16 | | | IV | + | − |
| 17 | | 3 | Ic | + | + |
| 18 | Serous papillary adenocarcinoma (carcinoma sparse necrosis) | — | IIIa | + | + |
| 19 | Serous papillary adenocarcinoma | 3 | Ic | + | + |
| 20 | | | Ib | + | + |
| 21 | | | | − | + |
| 22 | | 2 | IIb | + | + |
| 23 | | | Ia | + | + |
| 24 | | | IIb | + | + |
| 25 | | | Ib | + | + |
| 26 | Mucinous papillary adenocarcinoma | 3 | | + | − |
| 27 | | | Ia | + | + |
| 28 | | | IIa | + | + |
| 29 | | | Ib | + | + |
| 30 | Serous papillary adenocarcinoma | 2 | Ia | + | + |
| 31 | | | IIa | + | + |
| 32 | | — | Ib | + | + |
| 33 | | 3 | Ia | + | + |
| 34 | | 2 | IIIc | + | + |
| 35 | | 2-3 | II | + | + |
| 36 | Mucinous papillary adenocarcinoma | 2 | I | + | + |
| 37 | Mucinous papillary adenocarcinoma (tumoral necrosis) | — | Ib | − | − |

TABLE 6

| | OV20811 | Grade | Stage | orb | 253W |
|---|---|---|---|---|---|
| 38 | Serous papillary adenocarcinoma | 3 | IIa | + | + |
| 39 | | | IV | + | + |
| 40 | | | | + | + |
| 41 | | 2 | Ib | + | + |
| 42 | | 2-3 | Ia | − | + |
| 43 | Serous papillary adenocarcinoma (fibrous tissue and blood vessel) | — | IIIc | + | + |
| 44 | Serous papillary adenocarcinoma | 3 | IV | + | + |
| 45 | Mucinous papillary adenocarcinoma | | IIIc | + | + |
| 46 | Serous papillary adenocarcinoma | | | + | + |
| 47 | | | Ia | + | + |
| 48 | | — | | + | + |
| 49 | | 1 | IIIb | + | + |
| 50 | | 3 | Ia | + | + |
| 51 | | | IIb | + | + |
| 52 | Serous adenocarcinoma | 2 | II | + | + |
| 53 | Serous papillary adenocarcinoma | 3 | Ia | + | + |
| 54 | | 2 | | + | + |
| 55 | | 3 | IIa | + | + |
| 56 | Mucinous papillary adenocarcinoma | | Ia | + | + |
| 57 | Serous papillary adenocarcinoma | | II | + | + |
| 58 | Serous adenocarcinoma | 2 | IIIc | + | + |
| 59 | Serous papillary adenocarcinoma | 3 | Ib | + | + |
| 60 | Serous papillary adenocarcinoma | | IIIc | + | + |
| 61 | Mucinous papillary adenocarcinoma with necrosis | | Ia | + | + |
| 62 | Serous papillary adenocarcinoma | | IIa | + | + |
| 63 | | | Ia | + | + |
| 64 | | — | IIa | + | + |
| 65 | Serous adenocarcinoma | 3 | Ia | + | + |

TABLE 6-continued

| OV20811 | | Grade | Stage | orb | 253W |
|---|---|---|---|---|---|
| 66 | Serous papillary adenocarcinoma | | II | + | + |
| 67 | | | II | + | + |
| 68 | | | Ib | + | + |
| 69 | | | Ic | + | + |
| 70 | | 2 | Ia | + | + |
| 71 | Mucinous papillary adenocarcinoma | 3 | | + | + |
| 72 | Mucinous papillary adenocarcinoma (corpus albicans tissue) | — | Ib | + | + |
| 73 | Serous papillary adenocarcinoma (fibrous tissue) | — | Ia | + | + |
| 74 | Serous papillary adenocarcinoma | 3 | III | + | + |

TABLE 7

| OV20811 | | Grade | Stage | orb | 253W |
|---|---|---|---|---|---|
| 75 | Serous papillary adenocarcinoma (ovary tisuue) | — | Ic | − | + |
| 76 | Serous papillary adenocarcinoma | 3 | IIa | + | + |
| 77 | | | | + | + |
| 78 | | | IIb | + | + |
| 79 | Mucinous papillary adenocarcinoma with necrosis | | II | + | + |
| 80 | Serous papillary adenocarcinoma | | Ib | + | + |
| 81 | | | | + | + |
| 82 | Serous papillary adenocarcinoma (ovary tisuue) | — | II | + | + |
| 83 | Serous papillary adenocarcinoma | 3 | Ia | + | + |
| 84 | Serous papillary adenocarcinoma (chronic inflammation of fibrous tissue and blood vessel) | — | | + | + |
| 85 | Serous papillary adenocarcinoma | 3 | Ib | + | + |
| 86 | | | I | + | + |
| 87 | | | Ia | + | + |
| 88 | Serous papillary adenocarcinoma with necrosis | | I | + | + |
| 89 | Serous papillary adenocarcinoma | 2 | | + | + |
| 90 | | 3 | II | + | + |
| 91 | | | Ic | − | + |
| 92 | Mucinous papillary adenocarcinoma with necrosis | | Ib | + | + |
| 93 | Adenocarcinoma (sparse) | — | III | − | + |
| 94 | Serous papillary adenocarcinoma | 3 | I | + | + |
| 95 | | | Ia | + | + |
| 96 | Mucinous papillary adenocarcinoma | | Ib | + | + |
| 97 | Mucinous adenocarcinoma | | IIa | − | + |
| 89 | | | Ib | + | + |
| 99 | Adenocarcinoma | | Ia | + | + |
| 100 | | | II | + | + |
| 101 | | 2 | Ia | + | + |
| 102 | Endometrioid adenocarcinoma | 1 | Ib | + | + |
| 103 | Endometrioid adenocarcinoma (tumoral necrosis) | — | II | − | − |
| 104 | Endometrioid adenocarcinoma | 1 | | + | + |
| 105 | Endometrioid adenocarcinoma (tumoral necrosis) | — | Ic | − | − |

TABLE 8

| OV20811 | | Grade | Stage | orb | 253W |
|---|---|---|---|---|---|
| 106 | Endometrioid adenocarcinoma | 1 | Ia | + | + |
| 107 | Endometrioid adenocarcinoma (sparse) | | IIa | − | + |
| 108 | Endometrioid adenocarcinoma | | Ia | + | + |
| 109 | | | I | − | + |
| 110 | | | | + | + |
| 111 | | | Ib | + | + |
| 112 | | | Ia | + | + |
| 113 | | | IIa | + | + |
| 114 | | | I | + | + |
| 115 | | | Ia | + | + |
| 116 | | 3 | I | + | + |
| 117 | | 2 | Ia | + | + |
| 118 | | | I | + | + |
| 119 | | 3 | IIa | + | + |
| 120 | | | IV | + | + |
| 121 | | 2 | Ic | + | + |
| 122 | | | IIc | + | + |
| 123 | | 3 | Ia | + | + |
| 124 | | | Ic | + | + |
| 125 | | | Ib | + | + |
| 126 | | | IIa | + | + |
| 127 | Clear cell carcinoma | — | I | − | − |
| 128 | | | | + | + |
| 129 | Clear cell carcinoma (sparse) with massive necrosis | | IIIc | − | + |
| 130 | Clear cell carcinoma (sparse) with necrosis | | I | + | + |
| 131 | Clear cell carcinoma | | | + | + |
| 132 | | | | + | + |
| 133 | Clear cell carcinoma (tumoral necrosis) | | II | − | − |
| 134 | Clear cell carcinoma | | Ic | + | + |
| 135 | | | I | + | + |
| 136 | | | | + | + |
| 137 | Undifferentiated carcinoma | | | + | + |
| 138 | | | Ia | + | + |
| 139 | Squamous cell carcinoma | 1 | I | + | + |
| 140 | from malignant transformation | 2 | Ia | + | + |
| 141 | of teratoma | | IIa | + | + |
| 142 | | | IIIc | + | + |
| 143 | | | Ia | + | + |
| 144 | | 3 | | + | + |

TABLE 9

| OV20811 | | Grade | Stage | orb | 253W |
|---|---|---|---|---|---|
| 145 | Squamous cell carcinoma | — | Ib | + | + |
| 146 | Transitional cell carcinoma | | | + | + |

TABLE 9-continued

| | OV20811 | Grade | Stage | orb | 253W |
|---|---|---|---|---|---|
| 147 | | | IIIc | + | + |
| 148 | | | Ia | − | + |
| 149 | | | | + | + |
| 150 | Endodermal sinus carcinoma | | | − | + |
| 151 | | | IV | − | + |
| 152 | | | Ic | − | − |
| 153 | | | | − | + |
| 154 | | | Ib | − | + |
| 155 | | | I | − | + |
| 156 | | | | − | + |
| 157 | | | II | + | + |
| 158 | | | Ib | − | + |
| 159 | | | II | − | + |
| 160 | | | Ib | − | + |
| 161 | | | IV | − | − |
| 162 | | | Ia | + | − |
| 163 | | | | + | − |
| 164 | Granular cell tumor | | I | − | + |
| 165 | | | Ic | − | + |
| 166 | | | Ib | − | − |
| 167 | | | I | − | + |
| 168 | | | Ia | − | + |
| 169 | | | Ib | − | − |
| 170 | | | Ia | − | + |
| 171 | | | IIb | + | − |
| 172 | | | Ic | − | − |
| 173 | | | I | − | + |
| 174 | | | Ia | − | − |
| 175 | | | | − | − |
| 176 | | | | − | + |
| 177 | | | | + | + |
| 178 | | | | − | − |

TABLE 10

| | OV20811 | Grade | Stage | orb | 253W |
|---|---|---|---|---|---|
| 179 | Granular cell tumor | — | Ib | + | − |
| 180 | | | | − | − |
| 181 | | | Ia | − | − |
| 182 | | | II | − | + |
| 183 | | | Ib | N.T. | + |
| 184 | Dysgerminoma | | Ia | + | + |
| 185 | | | Ib | + | + |
| 186 | | | Ia | + | + |
| 187 | | | | + | + |
| 188 | | | | + | − |
| 189 | | | IIb | + | + |
| 190 | | | Ia | − | − |
| 191 | | | I | − | + |
| 192 | | | Ia | − | − |
| 193 | | | | + | + |
| 194 | Interstitial cell tumor | | | − | − |
| 195 | Sertoli cell tumor | | | + | + |
| 196 | | | Ic | − | − |
| 197 | | | I | − | − |
| 198 | Theca cell tumor | | Ia | − | − |
| 199 | | | | − | − |
| 200 | Malignant theca cell | | Ib | − | + |
| 201 | tumor | | III | − | − |
| 202 | Malignant teratoma | | Ia | − | + |
| 203 | Immature teratoma | | Ib | − | − |
| 204 | | | | − | − |
| 205 | | | I | − | − |
| 206 | Gynandrobiastoma | | Ia | − | − |
| 207 | Malignant fibroepithelioma | | | − | − |
| 208 | Malignant non-specificity steroid cell tumor | | | − | − |

TABLE 11

| | OV2088 | Grade | Stage | orb | 253W |
|---|---|---|---|---|---|
| 1 | Serous papillary adenocarcinoma | 1 | Ia | + | + |
| 2 | | | | + | + |
| 3 | | 2 | Ib | + | + |
| 4 | | | | − | − |
| 5 | | 1 | Ia | − | + |
| 6 | | | | − | + |
| 7 | | 2 | Ib | + | + |
| 8 | | | | + | + |
| 9 | | 1 | Ia | − | − |
| 10 | | | | − | − |
| 11 | | | | − | + |
| 12 | | | | − | + |
| 13 | | | | − | − |
| 14 | Serous papillary adenocarcinoma (fibrous tissue and blood vessel) | — | | − | − |
| 15 | Serous papillary adenocarcinoma | 1 | Ic | − | − |
| 16 | | | | − | − |
| 17 | Serous adenocarcinoma | 2 | I | + | + |
| 18 | | | | + | + |
| 19 | Serous papillary adenocarcinoma | 1 | | + | + |
| 20 | | | | − | + |
| 21 | | | Ia | − | + |
| 22 | | | | + | + |
| 23 | | 2 | Ic | − | + |
| 24 | | | | + | + |
| 25 | | | III | − | − |
| 26 | | | | − | − |
| 27 | | | | − | + |
| 28 | | | | − | + |
| 29 | | | Ia | − | + |
| 30 | | | | − | − |
| 31 | | | | − | − |
| 32 | | | | − | − |
| 33 | | | Ib | + | + |
| 34 | | | | + | + |
| 35 | Serous adenocarcinoma with necrosis | | IIIa | − | − |
| 36 | Serous adenocarcinoma (sparse) | | | + | − |
| 37 | Serous papillary adenocarcinoma | | I | + | + |
| 38 | | | | + | + |
| 39 | | | Ib | + | + |
| 40 | | | | + | − |

TABLE 12

| | OV2088 | Grade | Stage | orb | 253W |
|---|---|---|---|---|---|
| 41 | Serous adenocarcinoma (sparse) | 2 | Ib | − | − |
| 42 | Serous adenocarcinoma (fibrous tissue and blood vessel) | — | | − | − |
| 43 | Serous adenocarcinoma | 3 | Ia | − | − |
| 44 | | | | − | − |
| 45 | | 2 | | − | + |
| 46 | | | | − | + |
| 47 | Serous adenocarcinoma (fibrous tissue and blood vessel) | — | | − | − |
| 48 | | | | − | − |
| 49 | Serous adenocarcinoma | 3 | Ib | + | + |
| 50 | | | | + | + |
| 51 | Serous adenocarcinoma (ovarian tissue) | — | | + | + |
| 52 | | | | − | + |
| 53 | Serous papillary adenocarcinoma | 3 | Ia | − | + |
| 54 | | | | − | + |
| 55 | | 2 | II | + | + |
| 56 | | | | + | + |
| 57 | | 3 | Ib | − | + |
| 58 | | | | − | + |
| 59 | | 2 | | + | + |
| 60 | | | | + | − |
| 61 | | | III | − | − |
| 62 | | | | − | − |
| 63 | | | I | + | + |
| 64 | | | | − | + |
| 65 | Serous adenocarcinoma (necrotic tissue) | — | | − | − |
| 66 | | | | − | − |
| 67 | Serous adenocarcinoma | 3 | Ib | − | + |

TABLE 12-continued

| | OV2088 | Grade | Stage | orb | 253W |
|---|---|---|---|---|---|
| 68 | | | | + | + |
| 69 | | | | + | + |
| 70 | Serous papillary adenocarcinoma (fibrous tissue and blood vessel) | — | | + | + |
| 71 | Serous adenocarcinoma (necrotic tissue) | | Ic | − | + |
| 72 | Serous adenocarcinoma | 3 | | − | + |
| 73 | | | III | − | + |
| 74 | | | | − | − |
| 75 | | | II | + | + |
| 76 | | | | + | + |
| 77 | | | Ic | − | + |
| 78 | | | | − | + |
| 79 | | | Ia | − | + |
| 80 | | | | − | + |

TABLE 13

| | OV2088 | Grade | Stage | orb | 253W |
|---|---|---|---|---|---|
| 81 | Serous adenocarcinoma | 3 | IIc | + | + |
| 82 | | | | + | + |
| 83 | | | Ia | + | + |
| 84 | | | | − | + |
| 85 | | 2 | Ib | + | + |
| 86 | Serous adenocarcinoma (ovarian tissue) | — | | + | + |
| 87 | Serous adenocarcinoma | 3 | II | + | + |
| 88 | | | | + | + |
| 89 | | | I | − | + |
| 90 | | | | − | + |
| 91 | | | II | − | + |
| 92 | | | | − | + |
| 93 | | | IV | + | − |
| 94 | | | | + | + |
| 95 | | | II | − | + |
| 96 | | | | − | + |
| 97 | | | IIa | − | + |
| 89 | | | | − | + |
| 99 | | | Ia | − | − |
| 100 | | | | + | + |
| 101 | Serous adenocarcinoma (chronic inflammation of fibrous tissue and blood vessel) | — | | + | + |
| 102 | Serous adenocarcinoma | 3 | | + | + |
| 103 | Serous adenocarcinoma (fibrous tissue and blood vessel) | — | Ic | + | + |
| 104 | | | | − | + |
| 105 | Serous adenocarcinoma | 3 | Ic | + | + |
| 106 | | | | − | − |
| 107 | Serous papillary adenocarcinoma | | Ib | − | − |
| 108 | | | | − | − |
| 109 | Serous adenocarcinoma | | Ia | − | − |
| 110 | | | | − | − |
| 111 | | | Ib | − | + |
| 112 | Serous adenocarcinoma (ovarian tissue) | — | | − | + |
| 113 | Serous adenocarcinoma | 3 | Ia | + | − |
| 114 | | | | + | − |
| 115 | | | I | − | − |
| 116 | | | | − | + |
| 117 | | | | − | + |
| 118 | | | | − | + |
| 119 | | | | − | + |
| 120 | | | | − | − |

TABLE 14

| | OV2088 | Grade | Stage | orb | 253W |
|---|---|---|---|---|---|
| 121 | Serous adenocarcinoma with clear cell carcinoma | 3 | Ia | − | + |
| 122 | | | | − | − |
| 123 | Mucinous papillary adenocarcinoma | 1 | I | − | − |
| 124 | | | | − | − |
| 125 | | 2 | Ic | − | − |
| 126 | | | | − | + |
| 127 | Serous papillary adenocarcinoma | 1-2 | II | − | − |
| 128 | | | | − | − |
| 129 | Mucinous papillary adenocarcinoma | 1 | I | + | + |
| 130 | | | | + | + |
| 131 | | | Ia | + | + |
| 132 | | | | + | + |
| 133 | | 1-2 | | + | + |
| 134 | | | | + | + |
| 135 | Mucinous adenocarcinoma | 2 | | − | − |
| 136 | | | | − | − |
| 137 | | | I | − | − |
| 138 | | | | − | − |
| 139 | Adenocarcinoma | 3 | Ia | − | − |
| 140 | | | | − | − |
| 141 | Adenocarcinoma from malignant transformation of teratoma | | | − | − |
| 142 | | | | − | − |
| 143 | Adenocarcinoma | | | − | − |
| 144 | | | | − | − |
| 145 | Endometrioid carcinoma | — | Ib | + | + |
| 146 | (sparse) | | | + | + |
| 147 | Squamous cell carcinoma from malignant transformation | | IIIc | N.T. | N.T. |
| 148 | of teratoma (mature teratoma sparse) | | | + | + |
| 149 | Squamous celll carcinoma from malignant transformation | 3 | Ib | − | − |
| 150 | of teratoma | | | − | − |
| 151 | Squamous celll carcinoma | | | − | + |
| 152 | | | | − | + |
| 153 | Squamous cell carcinoma from malignant transformation | | Ia | + | − |
| 154 | of teratoma | | | + | − |
| 155 | Endodermal sinus carcinoma | — | | − | + |
| 156 | | | | − | + |
| 157 | | | Ib | − | + |
| 158 | | | | − | + |
| 159 | | | | − | − |
| 160 | | | | − | − |

TABLE 15

| | OV2088 | Grade | Stage | orb | 253W |
|---|---|---|---|---|---|
| 161 | Endometrioid carcinoma | 2 | Ia | + | + |
| 162 | | | | + | + |
| 163 | Granular cell tumor | — | | − | − |
| 164 | | | | − | + |
| 165 | | | | + | + |
| 166 | | | | + | + |
| 167 | | | Ib | − | − |
| 168 | | | | + | + |
| 169 | | | | − | − |
| 170 | | | | − | − |
| 171 | Granulosa-theca cell tumor | | | − | − |
| 172 | | | | − | − |
| 173 | Granular cell tumor | | | − | − |
| 174 | | | | − | − |
| 175 | | | Ia | − | + |
| 176 | | | | − | + |
| 177 | | | | + | − |
| 178 | | | | + | − |
| 179 | Clear cell carcinoma | 2 | I | + | + |
| 180 | | | | + | + |
| 181 | | 3 | | + | + |
| 182 | | | | + | + |
| 183 | Clear cell carcinoma with necrosis | 2 | IIIc | + | + |
| 184 | | | | − | − |
| 185 | Dysgerminoma | — | I | − | + |
| 186 | | | | − | + |

TABLE 15-continued

| | OV2088 | Grade | Stage | orb | 253W |
|---|---|---|---|---|---|
| 187 | | | Ia | + | + |
| 188 | | | | + | + |
| 189 | | | Ib | – | – |
| 190 | | | | – | – |
| 191 | Immature teratoma | | | – | + |
| 192 | | | | – | – |
| 193 | | | Ia | – | + |
| 194 | | | | – | – |
| 195 | Strumal carcinoid (sparse) | | Ib | + | + |
| 196 | | | | + | + |
| 197 | Undifferentiated carcinoma | | | + | – |
| 198 | with neruoendocrine feature | | | + | – |
| 199 | Transitional cell carcinoma | 2 | | + | + |
| 200 | | | | + | N.T. |

TABLE 16

| | OV2088 | Grade | Stage | orb | 253W |
|---|---|---|---|---|---|
| 201 | Carcinosarcoma | — | Ia | – | – |
| 202 | | | | – | – |
| 203 | Cellular fibroma | — | | – | – |
| 204 | | | | – | – |
| 205 | Embryonal carcinoma | | Ia | – | – |
| 206 | | | | N.T. | N.T. |
| 207 | Diffuse B-cell lymphoma | — | | – | – |
| 208 | | | | – | – |

TABLE 17

| | | FDA800a | orb | 253W |
|---|---|---|---|---|
| 1 | Skin | Basal cell carcinoma of occipitalia skin | + | – |
| 2 | | Squamous cell carcinoma of left chest wall | + | – |
| 3 | Lung | Small cell carcinoma | – | – |
| 4 | | Adenocarcinoma | + | – |
| 5 | | Squamous cell carcinoma | – | + |
| 6 | | Large cell carcinoma | + | + |
| 7 | | Bronchoalveolar carcinoma | – | – |
| 8 | Testis | Spermatocytoma | + | – |
| 9 | | Spermatocytoma | – | – |
| 10 | | Embryonal carcinoma | + | + |
| 11 | Prostate | Adenocarcinoma (Gleason grade: 4; Gleason score: 4 + 5) | + | + |
| 12 | | Rhabdomyosarcoma | – | – |
| 13 | Gall | Adenocarcinoma | + | + |
| 14 | bladder | Adenosquamous carciinoma | + | – |
| 15 | Small | Adenocarcinoma | + | – |
| 16 | intestine | Low garde malignant interstitialoma | – | + |
| 17 | Pancreas | Duct Adenocarcinoma | + | + |
| 18 | | Islet cell carcinoma | – | + |
| 19 | Colon | Adenocarcinoma | + | + |
| 20 | | Low garde malignant interstitialoma | + | + |
| 21 | Rectum | Adenocarcinoma | + | + |
| 22 | | Low garde malignant interstitialoma | – | – |
| 23 | | Malignant melanoma | + | + |
| 24 | Esophagus | Squamous cell carcinoma | + | + |
| 25 | | Adenocarcinoma | + | – |
| 26 | Appendix | Adenocarcinoma | + | + |
| 27 | Tongue | Squamous cell carcinoma | + | + |
| 28 | Parotid gland | Adenoid cystic carcinoma | + | + |
| 29 | Stomach | Mucinous adenocarcinoma | + | + |
| 30 | Liver | Hepatoblastoma | + | – |
| 31 | | Hepatocellular carcinoma | + | + |
| 32 | Breast | Ductal carcinoma in situ | + | + |
| 33 | | Invasive ductal carcinoma | + | + |
| 34 | | Duvtal carcinoma in situ | + | – |
| 35 | | Medullary carcinoma | N.T. | N.T. |
| 36 | Uterus | Adenocarcinoma endometrium | + | + |

TABLE 17-continued

| | | FDA800a | orb | 253W |
|---|---|---|---|---|
| 37 | | Clear cell carcinoma with necrosis (sparse) | + | + |
| 38 | | Leiomyoma | – | – |
| 39 | | Squamous cell carcinoma | + | + |
| 40 | Cervix | Endocervical type adenocarcinoma | + | + |

TABLE 18

| | | FDA800a | orb | 253W |
|---|---|---|---|---|
| 41 | Ovary | Mucinous adenocarcinoma | – | + |
| 42 | | Serous adenocarcinoma | + | + |
| 43 | Mediastinum | Thymoma (type B3) | + | + |
| 44 | Thyroid | Medullary carcinoma | – | – |
| 45 | | Papilly carcinoma | + | + |
| 46 | Brain | Atypical meningioma | – | + |
| 47 | | Malignant ependymoma of right occipital lobe | – | – |
| 48 | | Anaplastic oligodenoglioma with calcification (sparse) | – | – |
| 49 | | Pantmorphic glioblastoma of right occipital lobe | + | + |
| 50 | | Medulloblastoma of cerebullum | – | – |
| 51 | Bladder | Transitional cell carcinoma | – | – |
| 52 | | Low garde malignant leiomysarcoma | + | – |
| 53 | Kidney | Transitional cell carcinoma | – | – |
| 54 | | Papillary renal cell carcinoma | – | – |
| 55 | | Clear cell carcinoma | – | – |
| 56 | Lymph node | Diffuse B-cell lymphoma | + | – |
| 57 | | Diffuse B-cell lymphoma of right thigh | – | – |
| 58 | | Diffuse B-cell lymphoma of mandible | – | – |
| 59 | | Diffuse B-cell lymphoma of spleen | – | – |
| 60 | | Hodgkin's lymphoma of left clavicle | – | – |
| 61 | Soft tissue | Leiomyosarcoma of chest wall | – | – |
| 62 | | Embryonal rhabdomyosarcoma of left leg | – | – |
| 63 | Retroperitoneum | Rhabdomyosarcoma | – | – |
| 64 | | Primitive neuroectodennal tumor | – | – |
| 65 | Abdominal wall | Clear cell sarcoma | + | + |
| 66 | Retro-peritoneum | Neuroblastoma | – | – |
| 67 | Peritoneal cavity | Mucinous liposarcoma | – | – |
| 68 | Pelvic cavity | Chordoma | + | + |
| 69 | Soft tissue | Neurofibroma of right low back | N.T. | N.T. |
| 70 | Pelvic cavity | Synovial sarcoma of right chest wall | – | – |
| 71 | Bone | Osteosarcoma of right femur | – | – |
| 72 | Peritoneum | Malignant mesothelioma | – | – |

TABLE 19

| | | MC964a | orb | 253W |
|---|---|---|---|---|
| 1 | Cerebrum | Astrocytoma | + | – |
| 2 | | Anaplastic oligogendroglioma | – | – |
| 3 | | Malignant ependymoma | + | – |
| 4 | | Astrocytoma | + | – |
| 5 | | Astrocytoma | + | – |
| 6 | | Glioblastoma | + | + |
| 7 | Esophagus | Squamous cell carcinoma (sparse) | + | + |
| 8 | | Squamous cell carcinoma (sparse) | + | + |
| 9 | | Squamous cell carcinoma | + | + |
| 10 | Stomach | Adenocarcinoma | – | – |

TABLE 19-continued

| | | MC964a | orb | 253W |
|---|---|---|---|---|
| 11 | | Adenocarcinoma | + | + |
| 12 | | Interstitialoma | + | + |
| 13 | Liver | Hepatocellular carcinoma | + | + |
| 14 | | Cholangioma | + | + |
| 15 | | Hepatoblastoma | + | + |
| 16 | Small | Ad enocarcinoma | + | + |
| 17 | intestine | Diffuse B-cell lymphoma | − | − |
| 18 | | Interstitialoma | + | + |
| 19 | Colon | Adenocarcinoma | + | + |
| 20 | | Interstitialoma | − | + |
| 21 | | Diffuse B-cell lymphoma | − | − |
| 22 | Rectum | Adenocarcinoma | + | + |
| 23 | | Interstitialoma | + | + |
| 24 | | Interstitialoma | + | − |
| 25 | Pancreas | Islet cell carcinoma | + | + |
| 26 | | Adenocarcinoma | + | + |
| 27 | | Adenocarcinoma | + | + |
| 28 | Omentum | Metastatic adenocarcinoma | + | + |
| 29 | majus | Metastatic dysgerminoma | − | + |
| 30 | | Interstitialoma | − | − |
| 31 | Lung | Small cell undifferentiated carcinoma | − | − |
| 32 | | Small cell undifferentiated carcinoma | − | − |
| 33 | | Atypical carcinoid | + | − |
| 34 | | Squamous cell carcinoma | + | + |
| 35 | | Adenocarcinoma | + | + |
| 36 | | Squamous cell carcinoma | + | + |

TABLE 20

| | | MC964a | orb | 253W |
|---|---|---|---|---|
| 37 | Uterine | Squamous cell carcinoma a | + | + |
| 38 | cervix | Squamous cell carcinoma | + | + |
| 39 | | Squamous cell carcinoma | + | + |
| 40 | Uterus | Endometrioid adenocarcinoma | + | + |
| 41 | | Endometrioid adenocarcinoma | + | + |
| 42 | | Clear cell carcinoma | − | + |
| 43 | Breast | Invasive lobular carcinoma | + | − |
| 44 | | Invasive ductal carcinoma | − | + |
| 45 | | Cystosarcoma phyllodes | − | − |
| 46 | Ovary | Serous adenocarcinoma | − | − |
| 47 | | Serous adenocarcinoma | − | + |
| 48 | | Serous adenocarcinoma | + | + |
| 49 | Spleen | Diffuse B-cell lymphoma | + | − |
| 50 | | Diffuse non-Hodgkin's lymphoma | − | − |
| 51 | | Diffuse B-cell lymphoma | + | + |
| 52 | Prostate | Adenocarcinoma (Gleason grade: 3; Gleason score: 3 + 4) | + | + |
| 53 | | Adenocarcinoma (Gleason grade: 3; Gleason score: 3 + 3) | + | + |
| 54 | | Adenocarcinoma (Gleason grade: 3; Gleason score: 2 + 3) | − | + |
| 55 | Testis | Seminoma with necrosis | − | + |
| 56 | | Diffuse B-cell lymphoma | − | − |
| 57 | | Embryonal carcinoma | + | + |
| 58 | Kidney | Clear cell carcinoma | − | + |
| 59 | | Clear cell carcinoma | − | + |
| 60 | | Sarcomatoid carcinoma | − | − |
| 61 | Bladder | Transitional cell carcinoma | + | + |
| 62 | | Mucinous adenocarcinoma | + | + |
| 63 | | Leiomyosarcoma | + | + |

TABLE 21

| | | MC964a | orb | 253W |
|---|---|---|---|---|
| 64 | Lymph | Hodgkin's lymphoma of neck | + | + |
| 65 | node | Hodgkin's lymphoma of neck | − | + |
| 66 | | Diffuse B-cell lymphoma of left groin | − | − |
| 67 | | Diffuse B-cell lymphoma of light elbow joint | − | − |
| 68 | Mediastinum | Diffuse T-cell lymphoma of mediastinum | − | − |
| 69 | Mesentery | Diffuse B-cell lymphoma of mesentery | + | − |
| 70 | Bone | Osteosarcoma of left leg | + | + |
| 71 | | Osteosarcoma of right femur | − | + |
| 72 | | Osteosarcoma of right femur | − | + |
| 73 | | Dedifferentiation chondrosarcoma of pars sacralis | − | − |
| 74 | | Well-differentiated chondrosarcoma of right femur | + | + |
| 75 | | Mesenchymal chondrosarcoma of pars sacralis | + | − |
| 76 | Skin | Squamous cell carcinoma of cheek | + | + |
| 77 | Tongue | Squamous cell carcinoma of lip | + | + |
| 78 | Nose | Squamous cell carcinoma of nose | + | + |
| 79 | Tongue | Squamous cell carcinoma of pharynx | + | + |
| 80 | Larynx | Squamous cell carcinoma of larynx | + | + |
| 81 | | Squamous cell carcinoma of larynx | + | + |
| 82 | Pharynx | Diffuse B-cell lymphoma of pharynx | − | − |
| 83 | Pharynx | Squamous cell carcinoma of larynx | − | + |
| 84 | Nose | Squamous cell carcinoma of nasopharynx | − | − |
| 85 | Tongue | Squamous cell carcinoma | + | + |
| 86 | | Embryonal rhabdomyosarcoma | − | + |
| 87 | | Mucoepidermoid carcinoma | + | + |
| 88 | Fatty tissue | Mucoid liposarcoma of left leg | + | + |
| 89 | Fibrous | Isolated fibroma of chest wall | − | − |
| 90 | tissue | Fibrosarcoma of left forearm | + | + |
| 91 | Thyroid | Medullary carcinoma | + | + |
| 92 | | Papillary carcinoma | + | + |
| 93 | | Diffuse B-cell lymphoma | − | − |
| 94 | Skin | Malignant melanoma of anus margin | + | + |
| 95 | | Basal cell carcinoma of scalp | − | − |
| 96 | | Squamous cell carcinoma of left chest wall | + | + |

Example 9

The amount of CNGB3 in exosomes isolated from blood was measured to examine whether it is possible to distinguish a patient with a CNGB3 high expression disease from a person without a CNGB3 high expression disease. The following tests were performed with an approval of the Hamamatsu Medical University Institutional Review Board.

<Serum Sample>

Blood collected from two healthy persons (persons with no tumor, who have not been confirmed to be affected by any disease and are expected to be healthy) and patients from Hamamatsu Medical University School of Medicine (three patients with ovarian cancer, three patients with uterine cancer, three patients with breast cancer, one patient with cervical cancer, two patients with colon cancer, three patients with endometriosis, and one patient with uterine adenomyosis patient) was centrifuged and the obtained serum aliquots were stored at −80° C. The patients with uterine adenomyosis are patients who have developed both of endometriosis and fibroids.

<Exosome Separation>

The exosome was isolated from the serum using Exosome Isolation Kit (manufactured by Fujifilm Wako Pure Chemical Industries, Ltd.) according to the manufacturer's instruction. Specifically, first, the serum was centrifuged at 1,000×g at 4° C.° for 20 minutes, and the supernatant was recovered. The collected supernatant was centrifuged at 10,000×g at 4° C. for 30 minutes, and the supernatant was transferred to a new tube. Subsequently, 1.0 mL of the supernatant was mixed with exosome capture beads with a rotator at 4° C. for 180 minutes. Subsequently, after washing the capture beads, the exosome was eluted with 100 μL of an elution buffer and stored at −20° C.

<Peptide Synthesis>

As a biotinylated Z13 peptide (peptide consisting of L-amino acids) in which biotin bound to a Z13 peptide (VRRADNRPG: SIM ID NO: 3), one synthesized by GenScript Inc. was used.

<Avidin Blotting>

An exosome isolated from 800 μL of serum was mixed with a concentrated Laemmli buffer to prepare a measurement sample. The measurement sample was isolated by SDS-PAGE and then transferred to a PVDF membrane. The PVDF membrane was blocked in 5% BSA-containing TBST (0.1 v/v % Tween-20) at room temperature for 60 minutes. The PVDF membrane after blotting was washed and incubated overnight at 4° C.° in 1.0 μg/mL of biotinylated Z13 peptide-containing TBST. Thereafter, the membrane was washed with TBST, and subsequently incubated at room temperature for 60 minutes in 0.1 μg/mL TBST containing HRP (horseradish peroxidase)-binding avidin (manufactured by Thermo Fisher Scientific). The CNGB3 on the membrane was detected using a CCD camera system (manufactured by ATTO) and ECL prime (manufactured by GE Healthcare). Densitometry analysis was performed using an image analysis software "CS Analyzer 4" (manufactured by ATTO).

<Statistical Analysis>

All analysis was performed using a medial statistics software "GraphPad Prism 6" (manufactured by GraphPad Software Corporation).

The signal intensity of the band of CNGB 3 and the relative value thereof (relative value with the signal intensity of healthy person 1 being 1) obtained in the result of avidin blotting of each measurement sample are shown in Table 22. However, since breast cancer patients 1 and 2 could secure only a small amount of serum, exosomes isolated from 100 μL of serum were used, and a breast cancer patient 3 used exosomes isolated from 37.5 μL of serum. For this reason, the signal intensity of breast cancer patient samples was corrected by multiplying by the reciprocal of a serum use amount.

TABLE 22

| Subject sample | Signal intensity | Relative signal intensity |
| --- | --- | --- |
| Healthy person 1 | 1082305 | 1.00 |
| Healthy person 2 | 1188517 | 1.10 |

TABLE 22-continued

| Subject sample | Signal intensity | Relative signal intensity |
| --- | --- | --- |
| Ovarian cancer patient 1 | 4377691 | 4.04 |
| Ovarian cancer patient 2 | 3907260 | 3.61 |
| Ovarian cancer patient 3 | 3620987 | 3.35 |
| Uterine body cancer patient 1 | 2681313 | 2.48 |
| Uterine body cancer patient 2 | 2939504 | 2.72 |
| Uterine body cancer patient 3 | 14049406 | 12.98 |
| Breast cancer patient 1 | 18864576 | 17.43 |
| Breast cancer patient 2 | 41851784 | 38.67 |
| Breast cancer patient 3 | 20114133 | 18.58 |
| Uterine cervix cancer patient 1 | 3480924 | 3.22 |
| Large intestine cancer patient 1 | 6057912 | 5.60 |
| Large intestine cancer patient 2 | 2285673 | 2.11 |
| Endometriosis patient 1 | 13117100 | 12.75 |
| Endometriosis patient 2 | 4358049 | 4.24 |
| Endometriosis patient 3 | 3454806 | 3.36 |
| Uterine adenomyosis patient 1 | 5835780 | 5.67 |

As a result, in all the samples, a band of CNGB3 was detected, and it was confirmed that CNGB3 was contained in the exosomes. The CNGB3 amount of exosomes isolated from cancer patients, endometriosis patients and uterine adenomyosis patients was more than two times the exosomes isolated from healthy persons. From the result, it was confirmed that in exosomes isolated from the serum of patients with high expression of CNGB3 in disease-causing cells of the patients, such as tumor patients, endometriosis patients, and uterine adenomyosis patients, a significantly larger amount of CNGB3 is contained than in the exosomes isolated from serum, and therefore, by setting an appropriate reference value (cutoff value), it is possible to evaluate a possibility of onset of a CNGB3 high expression disease based on the amount of CNGB3 in the exosomes.

In addition, it was confirmed that CNGB3 was even present in the exosomes of the healthy persons, although a very small amount. This is presumably because a molecule having a high binding property to CNGB3 such as CNGB3-binding peptide was used to detect CNGB3 of exosomes in serum with a very high sensitivity. Since it was possible to detect exosomes including CNGB3 released from an extremely small amount of cancer cells in the bodies of the healthy persons, it could be expected that it is also possible to detect not only an advanced cancer but also an early cancer even in a case where the exosomes in serum are set as specimens by using a CNGB3-binding peptide.

The invention claimed is:

1. A cytocidal agent comprising:
a peptide consisting of the amino acid sequence represented by SEQ ID NO: 1, and
a site which selectively binds to a target molecule, the site being directly or indirectly linked via a linker to the peptide,
wherein the peptide consisting of the amino acid sequence represented by SEQ ID NO: 1 does not comprise an alanine linked to the C-terminal thereof.

2. The cytocidal agent according to claim 1, wherein the target molecule is a molecule present on a surface of a cell or a tissue.

3. The cytocidal agent according to claim 1,
wherein the peptide consisting of the amino acid sequence represented by SEQ ID NO: 1 is
a peptide exclusively consisting of L-amino acids,
a peptide in which, in the amino acid sequence represented by SEQ ID NO: 1, the first to the 14th amino acids are D-amino acids, and the 15th to 19th amino acids are L-amino acids,
a peptide in which, in the amino acid sequence represented by SEQ ID NO: 1, the first to 14th amino acids are L-amino acids, and the 15th to the 19th amino acids are D-amino acids, or
a peptide exclusively consisting of D-amino acids.

4. The cytocidal agent according to claim 1, wherein
the site selectively binding to the target molecule is a peptide or a protein, and
the peptide consisting of the amino acid sequence represented by SEQ ID NO: 1 and the site selectively binding to the target molecule are directly or indirectly linked to each other.

5. The cytocidal agent according to claim 1, wherein the target molecule is cyclic nucleotide-gated channel beta 3 (CNGB3) or annexin I.

6. The cytocidal agent according to claim 1, wherein
the site selectively binding to the target molecule is a peptide consisting of the amino acid sequence represented by SEQ ID NO: 2, and
the site selectively binding to the target molecule is directly or indirectly linked to a downstream of the peptide consisting of the amino acid sequence represented by SEQ ID NO: 1.

7. The cytocidal agent according to claim 1, wherein
the site selectively binding to the target molecule is a peptide consisting of the amino acid sequence represented by SEQ ID NO: 7, and
the peptide consisting of the amino acid sequence represented by SEQ ID NO: 1 is directly or indirectly linked downstream of the site selectively binding to the target molecule.

8. The cytocidal agent according to claim 1, which is a therapeutic agent of a disease resulting from abnormal proliferation of a cell.

9. The cytocidal agent according to claim 8, wherein the disease is endometriosis or cancer.

10. A method for treating a disease comprising a process in which an effective amount of a cytocidal agent is administered to an animal having a disease resulting from abnormal proliferation of a cell,
wherein the cytocidal agent comprising a peptide consisting of the amino acid sequence represented by SEQ ID NO: 1, and
a site which selectively binds to a target molecule, the site being directly or indirectly linked via a linker to the peptide,
wherein the peptide consisting of the amino acid sequence represented by SEQ ID NO: 1 does not comprise an alanine linked to the C-terminal thereof.

* * * * *